(12) United States Patent
Paranhos-Baccala et al.

(10) Patent No.: US 7,632,931 B2
(45) Date of Patent: Dec. 15, 2009

(54) ENDOGENEOUS NUCLEIC ACID FRAGMENT ASSOCIATED WITH AN AUTOIMMUNE DISEASE, LABELING METHOD AND REAGENT

(75) Inventors: Glaucia Paranhos-Baccala, Lyons (FR); Francois Mallet, Villeurbanne (FR); Cecile Voisset, London (GB)

(73) Assignee: Biomerieux, Marcy l'Etoile (FR)

( * ) Notice: Subject to any disclaimer, the term of this patent is extended or adjusted under 35 U.S.C. 154(b) by 189 days.

(21) Appl. No.: 10/632,793

(22) Filed: Aug. 4, 2003

(65) Prior Publication Data

US 2004/0048298 A1 Mar. 11, 2004

Related U.S. Application Data

(63) Continuation of application No. 09/869,927, filed as application No. PCT/FR00/00144 on Jan. 21, 2000, now abandoned.

(30) Foreign Application Priority Data

Jan. 21, 1999 (FR) .................................. 99 00888

(51) Int. Cl.
*C07H 21/02* (2006.01)
*C07H 21/04* (2006.01)
*C12Q 1/68* (2006.01)

(52) U.S. Cl. .................... 536/23.1; 536/24.3; 536/23.5; 435/6

(58) Field of Classification Search ........................ None
See application file for complete search history.

(56) References Cited

U.S. PATENT DOCUMENTS 5,474,796 A * 12/1995 Brennan .................... 427/2.13

FOREIGN PATENT DOCUMENTS

| EP | 0 731 168 | 9/1996 |
|---|---|---|
| FR | 2 737 500 | 2/1997 |
| FR | 2 765 588 | 1/1999 |
| WO | WO 93/07259 | 4/1993 |
| WO | WO 93/20188 | 10/1993 |
| WO | WO 94/28138 | 12/1994 |
| WO | WO 95/21256 | 8/1995 |
| WO | WO 98/23755 | 6/1998 |
| WO | WO 9823755 A1 * | 6/1998 |
| WO | WO 99/02696 | 1/1999 |

OTHER PUBLICATIONS

Blast 2 Sequence 'Align Seq ID 1:2, pp. 1-3.*
Mayer J et al 'Human endogenous retrovirus K homologous sequences and their coding capacity in Old World primates.' J Virol. Mar. 1998;72(3):1870-5.*
Chan E ' Integrating Transcriptomics and Proteomics'. Apr. 2006, Genetics and Proteomics, available online at www.genpromag.com, pp. 1-5.*
Newton MA 'On differential variability of expression ratios: improving statistical inference about gene expression changes from microarray data'. J Comput Biol. 2001;8(1):37-52.*
Lucentini J 'Gene Association Studies Typically Wrong' The Scientist (Dec. 20, 2004) p. 20.*
Thisted RA 'What is a P-value?' (1998) available online at http://www.stat.uchicago.edu?~thisted, pp. 1-6.*
P K Chanda and A K Banerjee 'Identification of promoter-proximal oligonucleotides and a unique dinucleotide, pppGpC, from in vitro transcription products of vesicular stomatitis virus.' J Virol. Jul. 1981; 39(1): 93-103.*
Perron H et al 'Molecular identification of a novel retrovirus repeatedly isolated from patients with multiple sclerosis. The Collaborative Research Group on Multiple Sclerosis.' Proc Natl Acad Sci U S A. Jul. 8, 1997;94(14):7583-8.*
Seifarth W et al 'Proviral structure, chromosomal location, and expression of HERV-K-T47D, a novel human endogenous retrovirus derived from T47D particles.' J Virol. Oct. 1998;72(10):8384-91.*
Zsigmond E. et al. Journal of Lipid Research, vol. 36, 1995, p. 1453-1462.*
Drwinga H.L. et al. NIGMS human/rodent somatic cell hybrid mapping panels 1 and 2. Genomics. May 1993;16(2):311-4. Absttract Only Provided.*
Sambrook, J., et al., Molecular Cloning, A Laboratory Manual, Cold Spring Harbor Laboratory Press, 1989.
Drwinga, H.L., et al., "NIGMS Human/Rodent Somatic Cell Hybrid Mapping Panels 1 and 2," Genomics, vol. 16, pp. 311-314, 1993.
Laemmli, U.K., "Cleavage of Structural Proteins during the Assembly of the Head of Bacteriophage T4," Nature, vol. 227, pp. 680-685, Aug. 15, 1970.
Towbin, H., et al., "Electrophoretic transfer of proteins from polyacrylamide gels to nitrocellulose sheets: Procedure and some applications," Proc. Natl. Acad. Sci. USA, vol. 76, No. 9, pp. 4350-4354, Sep. 1979.

* cited by examiner

Primary Examiner—Stephen Kapushoc
(74) Attorney, Agent, or Firm—Oliff & Berridge, PLC

(57) ABSTRACT

The invention concerns an endogenic nucleic fragment, such as an isolated retrovirus, integrated in the human DNA genome, the fragment being characterized in that it comprises, or consists of, at least part of the gag gene of an endogenetic retrovirus associated with an autoimmune disease or pregnancy failure or pregnancy pathologies, said part at least coding, directly and indirectly, for an expression product, or the complement of the fragment.

5 Claims, 5 Drawing Sheets

FIG 2A

```
              10         20         30         40         50
         1234567890 1234567890 1234567890 1234567890 1234567890
         CCTAGAACGT ATTCTGGAGA ATTGGGACCA ATGTGACACT CAGACGCTAA    50
         P  R  T  Y  S  G  E    L  G  P  M    H  S  D  A  K
          L  E  R  I  L  E  N  W  D  Q  C  D  T  Q  T  L  R
           .  N  V  F  W  R  I  G  T  N  V  T  L  R  R  .

GAAAGAAACG ATTTATATTC TTCTGCAGTA CCGCCTGGCC ACAATATCCT   100
         K  E  T  I  Y  I  L  L  Q  Y  R  L  A  T  I  S  S
          K  K  R  F  I  F  F  C  S  T  A  W  P  Q  Y  P
           E  R  N  D  L  Y  S  A  V  P  P  G  H  N  I  L

CTTCAAGGGA GAGAAACCTG GCTTCCTGAG GGAAGTATAA ATTATAACAT   150
          S  R  E    R  N  L  A  S  .  G  K  Y  K  L  .  H
         L  Q  G  R  E  T  W  L  P  E  G  S  I  N  Y  N  I
           F  K  G  E  K  P  G  F  L  R  E  V  .  I  I  T  S

CATCTTACAG CTAGACCTCT TCTGTAGAAA GGAGGGCAAA TGGAGTGAAG   200
         H  L  T  A  R  P  L  L  .  K  G  G  Q  M  E  .  S
          I  L  Q  L  D  L  F    C  R  K  E  G  K  W  S  E  V
           S  Y  S  .  T  S  S  V  E  R  R  A  N  G  V  K

TGCCATATGT GCAAACTTTC TTTTCATTAA GAGACAACTC ACAATTATGT   250
          A  I  C   A  N  F  L   F  I  K  R  Q  L    T  I  M
         P  Y  V  Q  T  F  F  S  L  R  D  N  S  Q  L  C
           C  H  M  C  K  L  S  F  H  .  E  T  T  H  N  Y  V

AAAAAGTGTG GTTTATGCCC TACAGGAAGC CCTCAGAGTC CACCTCCCTA   300
          K  V  W   F  M  P  Y  R  K  P   S  E  S  T  S  L
         K  K  C  G  L  C  P  T  G  S  P  Q  S  P  P  Y
           K  S  V  V  Y  A  L  Q  E  A  L  R  V  H  L  P  T

CCCCAGCGTC CCCTCCCCGA CTCCTTCCTC AACTAATAAG GACCCCCCTT   350
         P  Q  R  P    L  P  D  S  F  L  N  .  .  G  P  P  F
          P  S  V  P  S  P  T  P  S  S  T  N  K  D  P  P  L
           P  A  S  P  P  R  L  L  P  Q  L  I  R  T  P  L

TAACCCAAAC GGTCCAAAAG GAGATAGACA AAGGGGTAAA CAATGAACCA   400
         N  P  N    G  P  K  G  D  R  Q  R  G  K  Q  .  T  K
          T  Q  T  V  Q  K  E  I  D  K  G  V  N  N  E  P
           .  P  K  F  S  K  R  R  .  T  K  G  .  T  M  N  Q

AAGAGTGCCA ATATTCCCCG ATTATGCCCC CTCCAAGCAG TGAGAGGAGG   450
          E  C  Q  Y  S  P    I  M  P  P  P  S  S  E  R  R
         K  S  A  I  I  P  R  L  C  P  L  Q  A  V  R  G  G
           R  V  P  I  F  P  D  Y  A  P  S  K  Q  .  E  E  E

AGAATTCGGC CCAGCCAGAG TGCCTGTACC TTTTCTCTC TCAGACTTAA    500
         R  I  R  P    S  Q  S  A  C  T  F  F  S  L  R  L  K
          E  F  G  Q  A  R  V  P  V  P  F  S  L  S  D  L  K
           N  S  A  L  P  E  C  L  Y  L  F  L  S  Q  T  .
```

FIG 2B

```
               10         20         30         40         50
          1234567890 1234567890 1234567890 1234567890 1234567890
          AGCAAATTAA AATAGACCTA GGTAAATTCT CAGATAACCC TGACGGCTAT   550
           A  N  .  N  R  P  R  .  I  L  R  .  P  .  R  L  Y
            Q  I  K  I  D  L  G  K  F  S  D  N  P  D  G  Y
             S  K  L  K  .  T  .  V  N  S  Q  I  T  L  T  A  I

ATTGATGTTT TACAAGGGTT AGGACAATCC TTTGATCTGA CATGGAGAGA   600
           .  C  F  T  R  V  R  T  I  L  .  S  D  M  E  R
            I  D  V  L  Q  G  L  G  Q  S  F  D  L  T  W  R  D
             L  M  F  Y  K  G  .  D  N  P  L  I  .  H  G  E  I

TATAATGTTA CTACTAAATC AGACACTAAC CCCAAATGAG AGAAGTGCCG   650
           Y  N  V  T  T  K  S  D  T  N  P  K  .  E  K  C  R
            I  M  L  L  L  N  Q  T  L  T  P  N  E  R  S  A  A
             .  C  Y  Y  .  I  R  H  .  P  Q  M  R  E  V  P

CTGTAACTGC AGCCCGAGAG TTTGGCGATC TTTGGTATCT CAGTCAGGCC   700
           C  N  C  S  P  R  V  W  R  S  L  V  S  Q  S  G  Q
            V  T  A  A  R  E  F  G  D  L  W  Y  L  S  Q  A
             L  .  L  Q  P  E  S  L  A  I  F  G  I  S  V  R  P

AACAATAGGA TGACAACAGA GGAAAGAACA ACTCCCACAG GCCAGCAGGC   750
           Q  .  D  D  N  R  G  K  N  N  S  H  R  P  A  G
            N  N  R  M  T  T  E  E  R  T  T  P  T  G  Q  Q  A
             T  I  G  .  Q  Q  R  K  E  Q  L  P  Q  A  S  R  Q

AGTTCCCAGT GTAGACCCTC ATTGGGACAC AGAATCAGAA CATGGAGATT   800
           S  S  Q  C  R  P  S  L  G  H  R  I  R  T  W  R  L
            V  P  S  V  D  P  H  W  D  T  E  S  E  H  G  D  W
             F  P  V  .  T  L  I  G  T  Q  N  Q  N  M  E  I

GGTGCCACAA ACATTTGCTA ACTTGCGTGC TAGAAGGACT GAGGAAAACT   850
           V  P  Q  T  F  A  N  L  R  A  R  R  T  E  E  N  .
            C  H  K  H  L  L  T  C  V  L  E  G  L  R  K  T
             G  A  T  N  I  C  .  L  A  C  .  K  D  .  G  K  L

AGGAAGAAGC CTATGAATTA CTCAATGATG TCCACTATAA CACAGGGAAA   900
           E  E  A  Y  E  L  L  N  D  V  H  Y  N  T  G  K
            R  K  K  P  M  N  Y  S  M  M  S  T  I  T  Q  G  K
             G  R  S  L  .  I  T  Q  .  C  P  L  .  H  R  E  R

GGAAGAAAAT CTTACTGCTT TTCTGGACAG ACTAAGGGAG GCATTGAGGA   950
           G  R  K  S  Y  C  F  S  G  Q  T  K  G  G  I  E  E
            E  E  N  L  T  A  F  L  D  R  L  R  E  A  L  R  K
             K  K  I  L  L  L  F  W  T  D  .  G  R  H  .  G

AGCATACCTC CCTGTCACCT GACTCTATTG AAGGCCAACT AATCTTAAAG   1000
           A  Y  L  P  V  T  .  L  Y  .  R  P  T  N  L  K  G
            H  T  S  L  S  P  D  S  I  E  G  Q  L  I  L  K
             S  I  P  P  C  H  L  T  L  L  K  A  N  .  S  .  R
```

FIG 2C

```
           10         20         30         40         50
     1234567890 1234567890 1234567890 1234567890 1234567890
     GATAAGTTTA TCACTCAGTC AGCTGCAGAC ATTAGAAAAA ACTTCAAAAG    1050
      . V Y  H S V   S C R H   . K K   L Q K
     D K F  I T Q S   A A D   I R K N   F K S
      I S L  S L S Q   L Q .   L E K   T S K V

TCTGCCTTAG GCCCGGAGCA GAACTTAGAA ACCCTATTTA ACTTGGCATC    1100
     S A L G   P E Q   N L E   T L F N   L A S
     L P .   A R S R   T . K   P Y L   T W H P
      C L R   P G A   E L R N   P I .   L G I

CTCAGTTTTT TATAATAGAG ATCAGGAGGA GCAGGCGAAA CGGGACAAAC    1150
     S V F   Y N R D   Q E E   Q A K   R D K R
      Q F F   I I E   I R R S   R R N   G T N
     L S F L   . . R   S G G   A G E T   G Q T

GGGATAAAAA AAAAAGGGGG GGTCCACTAC TTTAGTCATG GCCCTCAGGC    1200
      D K K   K R G   G P L L   . S W   P S G
     G I K K   K G G   V H Y   F S H G   P Q A
     G . K   K K G G   S T T   L V M   A L R Q

AAGCAGACTT TGGAGGCTCT GCAAAAGGGA AAAGCTGGGC AAATCAAATG    1250
     K Q T L   E A L   Q K G   K A G Q   I K C
     S R L   W R L C   K R E   K L G   K S N A
      A D F   G G S   A K G K   S W A   N Q M

CCTAATAGGG CTGGCTTCCA GTGCGGTCTA CAAGGACACT TTAAAAAGA    1300
     L I G   L A S S   A V Y   K D T   L K K I
      . . G   W L P   V R S T   R T L   . K R
     P N R A   G F Q   C G L   Q G H F   K K D

TTATCCAAGT AGAAATAAGC CGCCCCCTTG TCCATGCCCC TTACGTCAAG    1350
      I Q V   E I S R   P L V   H A P   Y V K
     L S K .   K . A   A P L   S M P L   T S R
      Y P S   R N K P   P P C   P C P   L R Q G

GGAATCACTG GAAGGCCCAC TGCCCCAGGG GATGAAGATA CTCTGAGTCA    1400
     G I T G   R P T   A P G   D E D T   L S Q
     E S L   E G P L   P Q G   M K I   L . V R
      N H W   K A H   C P R G   . R Y   S E S

GAAGCCATTA ACCAGATGAT CCAGCAGCAG GACTGAGGGT GCCCGGGCG    1450
     K P L   T R . S   S S R   T E G   A R G E
      S H .   P D D   P A A G   L R V   P G A
     E A I N   Q M I   Q Q Q   D . G C   P G R

AGGGCCAGCC CATGCCATCA CCCTCACAGA GCCCGGGGTA TGTTTGACCA    1500
     R Q P   H P S   P S Q S   P G Y   V . P
      S A S P   C H H   P H R   A P G M   F D H
       A P A N   A I T   L T E   P R V   C L T I
```

FIG 2D

```
            10         20         30         40         50
   1234567890 1234567890 1234567890 1234567890 1234567890
   TTGAGACCA A                                              1511
   L  R  A
      E  P
   F  S  Q
```

ENDOGENEOUS NUCLEIC ACID FRAGMENT ASSOCIATED WITH AN AUTOIMMUNE DISEASE, LABELING METHOD AND REAGENT

CROSS REFERENCE TO RELATED APPLICATIONS

This is a Continuation of application Ser. No. 09/869,927, which is a U.S. National Stage Application of PCT/FR00/00144, filed Jan. 21, 2000. The entire disclosure of the prior applications is hereby incorporated by reference herein in its entirety.

The present invention relates to an endogenous nucleic acid fragment of the retroviral type, integrated into the DNA of the human genome.

FIELD OF THE INVENTION

Retroviruses are RNA viruses which replicate through a process termed reverse transcription, mediated by an RNA-dependent DNA polymerase named reverse transcriptase (RT), which is encoded by the pol gene. The retroviral RNA also comprises at least two additional genes, which are the gag and env genes. The gag gene encodes the proteins of the backbone, i.e. the matrix, the capsid and the nucleocapsid. The env gene encodes the envelope proteins. The transcription is regulated by promoter regions located in the LTRs (Long Terminal Repeat) which border the 5'- and 3'-terminal ends of the retroviral genome.

In the course of evolution, humans or their ancestors have integrated material of retroviral origin into their genome subsequent to an infection. Specifically, when a cell is infected, the reverse transcriptase makes a DNA copy of the retroviral RNA, and this DNA copy may then possibly integrate into the human genome. Retroviruses can infect germinal cells and thus be transmitted to future generations by vertical Mendelien transmission. They are then referred to as endogenous retroviruses which are present in the form of proviral DNA integrated into the genome of all human cells. Most endogenous retroviruses are silent or defective. However, some of them have been able to conserve all or part of their initial properties and may be activated under specific conditions. The expression of endogenous retroviruses can range from the transcription of viral genes to the production of viral particles.

These endogenous retroviruses may be associated directly or indirectly with the development of certain pathological conditions.

Endogenous retroviral structures may be in a complete LTR-gag-pol-env-LTR form or in truncated forms.

BACKGROUND OF THE INVENTION

Thus, in a previous patent application (PCT/FR98/01442; which corresponds to U.S. patent application Ser. No. 09/446,024), the applicant screened a cDNA library using a Ppol-MSRV probe (SEQ ID NO. 18) and detected overlapping clones which allowed it to reconstruct a putative genomic RNA of 7582 nucleotides. This genomic RNA has an R-U5-gag-pol-env-U3-R structure. A "blastn" interrogation over several databases using the reconstructed genome made it possible to show that there is a considerable amount of related genomic (DNA) sequences in the human genome, which are found on several chromosomes. Thus, the applicant demonstrated the existence of partial structures of the retroviral type in the human genome and envisaged their potential role in the development of autoimmune diseases, in unsuccessful pregnancy or pathological conditions of pregnancy.

Autoimmune diseases which may be mentioned by way of example are multiple sclerosis, rhumatoid arthritis, lupus erythematosus disseminatus, insulin-dependent diabetes and/or pathologies which are associated with them.

The isolation and sequencing of overlapping cDNA fragments and the identification of genomic (DNA) clones corresponding to the isolated DNA clones, described in the applicant's above-mentioned PCT and corresponding U.S. patent applications, are incorporated herein by way of reference.

Isolation and sequencing of overlapping cDNA fragments:

The information regarding the organization of the novel family of endogenous retroviruses named, by the applicant, HERV-W was obtained by testing a placenta cDNA library (Clontech cat#HL5014a) with the Ppol-MSRV (SEQ ID NO. 18) and Penv-C15 (SEQ ID NO. 19) probes and then carrying out a "gene walking" technique using the novel sequences obtained. The experiments were carried out with reference to the recommendations of the supplier of the library. PCR amplifications on DNA were also used in order to understand this organization.

The following clones were selected and sequenced:

Clone cl.6A2 (SEQ ID NO. 20): 5' untranslated region of HERV-W and a portion of gag.
Clone cl.6A1 (SEQ ID NO. 21): gag and a portion of pol.
Clone cl.7A16 (SEQ ID NO. 22): 3' region of pol.
Clone cl.Pi22 (SEQ ID NO. 23): 3' region of pol and start of env.
Clone cl.24.4 (SEQ ID NO. 24): spliced RNA comprising a portion of the 5' untranslated region of HERV-W, the end of pol and the 5' region of env.
Clone cl.C4C5 (SEQ ID NO. 25): end of env and 3' untranslated region of HERV-W.
Clone cl.PH74 (SEQ ID NO. 26): subgenomic RNA: 5' untranslated region of HERV-W, end of pol, env, and 3' untranslated region of HERV-W.
Clone cl.PH7 (SEQ ID NO. 27): multispliced RNA: 5' untranslated region of HERV-W, end of env and 3' untranslated region of HERV-W.
Clone cl.Pi5T (SEQ ID NO. 28): partial pol gene and U3-R region.
Clone cl.44.4 (SEQ ID NO. 29): R-U5 region, gag gene and partial pol gene.

A total sequence model for HERV-W was produced with the aid of these clones, by carrying out sequence alignments. The spliced RNAs were revealed and also the potential splice donor and acceptor sites. The LTR, gag, pol and env entities were defined by studying similarity with existing retroviruses.

The putative genetic organization of HERV-W in the RNA form is as follows (SEQ ID NO. 30):
gene 1..7582.

Location of the clones on the reconstructed genomic RNA sequence:
cl.6A2 (1321 bp) 1-1325;
cl.PH74 (535+2229=2764 bp) 72-606 and 5353-7582;
cl.24.4 (491+1457=1948 bp); 115-606 and 5353-6810;
cl.44.4 (2372 bp) 115-2496;
cl.PH7 (369+297=666 bp) 237-606 and 7017-7313; cl.6A1 (2938 bp) 586-3559;
cl.Pi5T (2785+566=3351 bp) 2747-5557 and 7017-7582;
cl.7A16 (1422 bp) 2908-4337;
cl.Pi22 (317+1689=2006 bp) 3957-4273 and 4476-6168;
cl.C4C5 (1116 bp) 6467-7582

| | |
|---|---|
| 5'LTR | 1..120<br>/note="R of 5'LTR (5' end uncertain"<br>121..575<br>/note="U5 of 5'LTR" |
| misc. | 579..596<br>/note="PBS, primer binding site, for tRNA-W" |
| misc. | 606<br>/note="splice junction (splice donor site ATCCAAAGTG-GTGAGTAATA (SEQ ID NO: 32) and splice acceptor site CTTTTTTCAG-ATGGGAAACG (SEQ ID NO: 33), clone RG083M05, GenBank accession AC000064)" |
| misc. | 5353<br>/note="splice acceptor site for ORF1 (env)" |
| misc. | 5560<br>/note="splice donor site" |
| ORF | 5581..7194<br>/note="ORF1 env 538 AA"<br>/product-="envelope" |
| misc. | 7017<br>/note="splice acceptor site for ORF2 and ORF3" |
| ORF | 7039..7194<br>/note="ORF2 52 AA" |
| ORF | 7112..7255<br>/note="ORF3 48 AA" |
| misc. | 7244..7254<br>/note"PPT, polypurine tract" |
| 3'LTR | 7256..7582<br>/note="U3-R of 3' LTR (U3-R junction undetermined) |
| misc. | 7563..7569<br>polyadenylation signal |

Identification of genomic (DNA) clones corresponding to the isolated DNA clones:

A "blastn" interrogation over several databases, using the reconstructed genome, showed that there is a considerable amount of related sequences in the human genome. Approximately 400 sequences were identified in GenBank and more than 200 sequences in the EST bank, most of them in the antisense orientation. The 4 most significant sequences in terms of size and similarity are the sequences of the following genomic (DNA) clones:

Human clone RG083M05 (gb AC000064), the chromosomal location of which is 7q21-7q22, Human clone BAC378 (gb U85196, gb AE000660) corresponding to the alpha/delta locus of the T-cell receptor, located at 14q11-12, Human cosmid Q11M15 (gb AF045450) corresponding to region 21q22.3 of chromosome 21, Cosmid U134E6 (embl Z83850) on chromosome Xq22.

The location of the aligned regions for each of the clones is indicated and the chromosome to which they belong is indicated between square brackets (FIG. 3 of the above-mentioned PCT and corresponding U.S. application, which corresponds to FIG. 1 herein). The percentage similarity (without the large deletions) between the 4 sequences and the reconstructed genomic RNA is indicated, as well as the presence of repeat sequences at each end of the genome and the size of the longest open reading frames (ORFs). Repeat sequences were found at the ends of 3 of these clones. The reconstructed sequence is entirely contained within clone RG083M05 (9.6 Kb) and exhibits 96% similarity. However, clone RG083M05 has a 2 Kb insertion located immediately downstream of the 5' untranslated region (5' UTR). This insertion is also found in two other genomic clones which have a 2.3 Kb deletion immediately upstream of the 3' untranslated region (3' UTR). No clone contained the three functional gag, pol and env open reading frames (ORFs). Clone RG083M05 shows a 538 amino acid (AA) ORF corresponding to a whole envelope. Cosmid Q11M15 contains two major contiguous ORFs of 413 AA (frame 0) and 305 AA (frame +1) corresponding to a truncated pol polyprotein.

BRIEF DESCRIPTION OF THE FIGURES

FIG. 2 sets forth the nucleotide sequence of clone C12 (SEQ ID NO: 1) and the corresponding potential amino acid reading frames (SEQ ID NOS: 34-36).

DETAILED DESCRIPTION OF THE INVENTION

Figure 1:
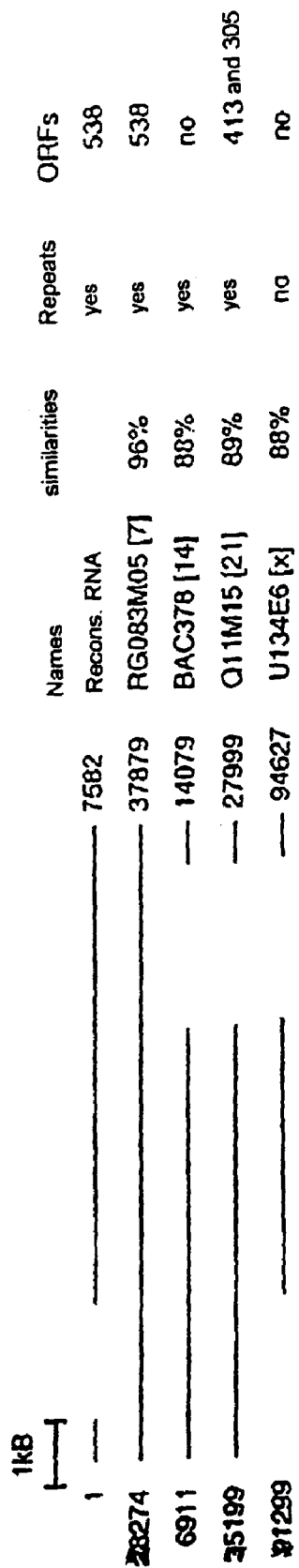
FIG. 1 sets forth the location of the aligned regions for the reconstructed genomic RNA and four clones. The chromosome to which each clone belongs is indicated in square brackets. Percentage similarity to the reconstructed genomic RNA is also indicated, as well as the presence or absence of repeat sequences, and the size of the longest open reading frame.

An endogenous nucleic acid fragment has now been found and isolated, which is integrated into the DNA of the human genome and which comprises or consists of at least one portion of the gag gene of an endogenous retrovirus associated with an autoimmune disease, or with unsuccessful pregnancy or pathological conditions of pregnancy, this portion at least encoding, directly or indirectly, an expression product. Of course, the invention also comprises the sequence complementary to said fragment.

Advantageously, the fragment defined above also satisfies at least any one of the following characteristics:

It comprises, or consists of, said whole gag gene;
Said portion of the fragment at least encodes the matrix and the capsid;
It comprises, or consists of, SEQ ID NO. 1, SEQ ID NO. 2, SEQ ID NO. 3 or the sequence complementary to any one of said sequences;
It is located on at least one of human chromosomes 1, 3, 6, 7 and 16, it is preferably located on at least chromosome 3;
The product of expression of said portion is messenger RNA;
The product of expression of said portion is immunologically recognized by antibodies present in a biological sample from a patient suffering from an autoimmune disease, such as multiple sclerosis; preferably, the biological fluid is chosen from serum, plasma, synovial fluid and urine.

Another subject of the invention is an endogenous transcription product which is in isolated form and which can be obtained by transcription of at least said portion of the gag gene of a fragment of the invention.

The invention also relates to a method for detecting endogenous nucleotide sequences belonging to a fragment of the invention, comprising the following steps:

a prior step of extraction of the cellular DNA from a tissue or biological fluid is carried out, and then at least one cycle of amplification of the cellular DNA is carried out, for instance by PCR, using primers in particular chosen from SEQ ID NO. 4 to SEQ ID NO. 9 and SEQ ID NO. 12 to SEQ ID NO. 17, the cellular DNA present in the sample is brought into contact with a given probe which is capable of hybridizing with a fragment as defined above and of forming a hybridization complex, said probe comprising at least 15 contiguous nucleotides, preferably 17 and advantageously 19 contiguous nucleotides, of SEQ ID NO. 3, or consisting of SEQ ID NO. 3, under suitable conditions for the hybridization, in particular under conditions of high stringency, and the hybridization complexes formed are detected by any suitable means.

Advantageously, the probe is labeled with a tracer, such as for example a radioactive tracer or an enzyme.

The invention also relates to a method for detecting endogenous nucleotide sequences belonging to a fragment of the invention, comprising the following steps:

a prior step of extraction of the cellular DNA from a tissue or biological fluid is carried out, and then at least one cycle of amplification of the cellular DNA is carried out, for instance by PCR, using primers in particular chosen from SEQ ID NO. 4 to SEQ ID NO. 9 and SEQ ID NO. 12 to SEQ ID NO. 17, a step of in vitro transcription/translation of the amplified product is carried out, and the product derived from the transcription/translation step is reacted with a serum or plasma from a patient with an autoimmune disease.

The invention also relates to a method for studying and/or monitoring T-cell proliferation in vitro, according to which the T cells from a patient are brought into contact with either transcription/translation products (SEQ ID NO. 31), as obtained according to the method above, or synthetic peptides derived from or belonging to SEQ ID NO. 31.

Another subject of the invention is a method for the in situ molecular labeling of chromosomes isolated from patients, in which a probe labeled with any suitable tracer, and comprising all or part of SEQ ID NO. 3, is used.

The invention also relates to:

a recombinant protein obtained using an expression cassette in a bacterial host, characterized in that its protein sequence consists of SEQ ID NO. 31; the bacterial host is in particular *E. coli*;

a reagent for detecting an autoimmune disease or monitoring pregnancy, comprising at least one fragment or one protein of the invention;

the use of a fragment or of a protein of the invention for detecting, in a biological sample, susceptibility to an autoimmune disease, or monitoring pregnancy; in particular, the autoimmune disease is multiple sclerosis.

Before setting out the present invention in greater detail, the definition of certain terms employed in the description and claims is given.

The expression "expression product" means any product derived from the retroviral DNA integrated into the human genome, including the transcription products (messenger RNA) and the products derived from the translation of the messenger RNA obtained. In the latter case, and by way of example, the product may be a peptide or a protein which is functional or functionalizable, i.e. which can become functional.

The expression "portion encoding, directly or indirectly, an expression product" is intended to mean a portion which, by itself, comprises at least all or part of an open reading frame from which it is possible to deduce an amino acid sequence, and the coding capacity of which can be induced by elements such as, for example, those which may have promoter activity. This definition includes the variability which may be found in the coding nucleic acid sequence, provided that the above conditions are respected.

EXAMPLE 1

Location of the gag Gene of the HERV-W Family on Human Chromosomes Using the Southern Blot Technique In order to locate the gag gene of the HERV-W family, a probe corresponding to this gene from MSRV was hybridized on a nylon membrane (Hybond® N+, Amersham) containing 5 μg of DNA from 24 somatic cell hybrids [human×rodents] (isolated human genomic DNA: 22 autosomal chromosomes and 2 sex chromosomes) and 3 control DNAs (human, mouse and hamster), digested with the EcoRI restriction enzyme.

The following probe is used: Pgag-C12 identified by SEQ ID NO. 3 corresponding to the coding region (of 1056 bp) of the clone MSRV gag C12.

1.1—Production of Clone 2, C12, Containing, in the 3' Region, a Portion Homologous to the pol Gene, Corresponding to the Protease Gene, and a Portion Homologous to the Gag Gene, Corresponding to the Nucleocapsid, and a 5' Coding Region, Corresponding to the gag Gene, More Specifically the Matrix and Capsid of MSRV-1.

A PCR amplification was carried out on total RNA extracted from 100 μl of plasma from a patient suffering from MS. A water control, treated under the same conditions, was used as a negative control. The cDNA synthesis was carried out with 300 pmol of a random primer (Gibco-BRL, France) and the "Expand RT" reverse transcriptase (Boehringer Mannheim, France), according to the conditions recommended by the company. A PCR (polymerase chain reaction) amplification was carried out with the Taq polymerase enzyme (Perkin Elmer, France) using 10 μl of cDNA under the following conditions: 94° C. 2 min, 55° C. 1 min and 72° C. 2 min, then 94° C. 1 min, 55° C. 1 min and 72° C. 2 min for 30 cycles and 72° C. for 7 min, with a final reaction volume of 50 μl.

The primers used for the PCR amplification are as follows:

```
5' primer, identified by SEQ ID NO. 4
5' CGG ACA TCC AAA GTG ATG GGA AAC G 3';

3' primer, identified by SEQ ID NO. 5
5' GGA CAG GAA AGT AAG ACT GAG AAG GC 3'
```

A second "nested" PCR amplification was carried out with 5' and 3' primers located inside the region already amplified. This second PCR was carried out under the same experiment conditions as those used in the first PCR, using 10 μl of the amplification product derived from the first PCR.

The primers used for the nested PCR amplification are as follows:

```
5' primer, identified by SEQ ID NO. 6
5' CCT AGA ACG TAT TCT GGA GAA TTG GG 3';

3' primer, identified by SEQ ID NO. 7
5' TGG CTC TCA ATG GTC AAA CAT ACC CG 3'
```

A 1511 bp amplification product was obtained from the RNA extracted from the MS patient plasma. The corresponding fragment was not observed for the water control. This amplification product was cloned in the following way.

The amplified DNA was inserted into a plasmid using the TA Cloning Kit®. The 2 μl of DNA solution were mixed with 5 μl of sterile distilled water, 1 μl of a 10× ligation buffer, 2 μl of PCR® vector (25 ng/ml) and 1 μl of T4 DNA ligase. This mixture was incubated overnight at 14° C. The following steps were carried out in accordance with the instructions of the TA Cloning® kit (Invitrogen). After transformation of the ligation in E. coli bacteria, the ligation mixture was plated out. At the end of the procedure, the white colonies of recombinant bacteria were picked in order to be cultured and to allow the extraction of the incorporated plasmids according to the "DNA minipreparation" procedure (J. Sambrook, E. F. Fritsch and T. Maniatis, Molecular Cloning, a laboratory manual, Cold Spring Harbour Laboratory Press, 1989). The plasmid preparation from each recombinant colony was cleaved with the Eco RI restriction enzyme and analyzed on agarose gel. The plasmids possessing an insert which was detected under UV light after staining the gel with ethidium bromide were selected in order to sequence the insert after hybridization with a primer complementary to the T7 promoter present on the cloning plasmid from the TA Cloning Kit®. The reaction prior to the sequencing was then carried out according to the method recommended for using the "Prism® Ready Reaction Amplitaq® FS, DyeDeoxy™ Terminator" sequencing kit (Applied Biosystems, ref. 402119) and the automatic sequencing was carried out on the Applied Biosystems 373 A and 377 machines, according to the manufacturer's instructions.

The clone obtained, named C12, makes it possible to define a 1511 bp region which has an open reading frame in the N-terminal region of 1056 bp (SEQ ID NO. 3) encoding 352 amino acids corresponding to the matrix and capsid regions of the gag gene.

The nucleotide sequence of C12 is identified by SEQ ID NO. 1. It is represented in FIG. 2 with the potential amino acid reading frames.

1.2—Production of the MSRV gag c12 Probe

The probe was obtained after PCR amplification, using the pCR™ vector plasmid (TA Cloning® kit, Invitrogen) containing the insert of the clone: MSRV gag c12, with the Taq polymerase (Perkin Elmer, France) under the following conditions: 94° C. 1 min, 55° C. 1 min and 72° C. 2 min for 35 cycles and 72° C. for 7 min, with a final reaction volume of 100 μl.

The primers used for the PCR amplification are as follows:

```
5' primer, identified by SEQ ID NO. 12
5'-CTA GAA CGT ATT CTG GAG AAT TGG GA-3'

3' primer, identified by SEQ ID NO. 13
5'-CCT AAG GCA GAC TTT TGA AG-3'.
```

A 1056 bp amplification product was obtained for MSRV gag c12.

After PCR amplification, the fragment was analyzed in 1% agarose gel. The fragment detected under UV light, after staining the gel with ethidium bromide, was cut out and labeled with [α-P$^{32}$] using random primers (Gibco-BRL, France) in accordance with instructions of the "Ready-to-go DNA labeling" kit (Pharmacia Biotech). The unincorporated nucleotides were removed with a G-50 Quick Spin column (Boehringer, Mannheim).

1.3—Southern Blot

The hybridization conditions are as follows:

After prehybridization for 4 hours (in 5×SSC, 1× Denhardt's, 0.1% SDS, 50% formamide, 20 mM Tris-HCl, pH=7.5, and 0.1 mg/ml of herring sperm DNA), the nylon membrane containing the human chromosomes was hybridized (in 5×SSC, 1× Denhardt's, 0.1% SDS, 50% formamide, 20 mM Tris-HCl, pH=7.5, 0.1 mg/ml of herring sperm DNA and 5% dextran sulfate) for 18 hours at 42° C. with the $^{32}$P-labeled 1056 bp gag c12 DNA probe (SEQ ID NO. 3). After hybridization, the membrane (The BIOS Monochromosomal Somatic Cell Hybrid blot, from Quantum Bioprobe) hybridized with the gag probe was washed twice in 2×SSC/0.2% SDS solution for 15 min at room temperature, and twice (in 0.2×SSC/0.2% SDS) for 15 min at 45° C. After washing, the membrane was exposed to the X-ray film at −80° C. in the presence of an amplifying screen.

The results are given in Table 1 hereinafter.

In this table:

m, which signifies mouse, and h, which signifies hamster, correspond to the recipient cells for the human chromosomal DNA.

The number indicated under each chromosome corresponds to the number of bands encountered.

The total number of copies of the gag gene is 66.

TABLE 1

| Chromo No. | 1 | 2 | 3 | 4 | 5 | 6 | 7 | 8 | 9 | 10 | 11 | 12 | 13 | 14 | 15 | 16 | 17 | 18 | 19 | 20 | 21 | 22 | X | Y | Mouse | Hamster |
|---|---|---|---|---|---|---|---|---|---|---|---|---|---|---|---|---|---|---|---|---|---|---|---|---|---|---|
| Rodent parent | m | h | h | h | h | h | h | h | h | h | h | h | h | h | h | m | m | h | h | m | m | h | h | h | | |
| Gag probe | 5 | 0 | 6 | 6 | 5 | 3 | 2 | 3 | 2 | 4 | 3 | 6 | 3 | 1 | 3 | 0 | 3 | 2 | 1 | 0 | 4 | 0 | 4 | 0 | 0 | 0 |

EXAMPLE 2

PCR Amplification of the gag Gene of the HERV-W Family on Each of the Isolated Human Chromosomes; Verification of the Specificity of the Amplifications by Southern Blot; "In vitro" Transcription/Translation (PTT) Test Using the PCR Products, in Order to Verify the Coding Capacity and Discover Which of the Human Chromosomes have Open Reading Frames for the gag Gene of the HERV-W Family 2.1—PCR Amplification In order to amplify the HERV-W gag gene, a PCR was carried out on each isolated human chromosome [NIGMS human/rodent somatic cell hybrid panel #2. The human monochromosomal NIGMS somatic hybrid mapping panel #2, described by H. L. Drwinga et al. and B. L. Dubois et al., obtained from the Coriell Institute (Camden, N.J.)] with the Taq polymerase enzyme (Perkin Elmer, France) using: 40 pmol of each primer, 25 mM of each dNTP (Pharmacia), 2.5 mM of MgCl$_2$, 2.5 U of Taq polymerase in the standard PCR buffer (Perkin Elmer) and 300 ng of isolated chromosome DNA, in a final volume of 100 μl. The PCR conditions for amplifying the gag region are as follows: 3 min at 94° C.; then 1 min at 94° C., 1 min at 55° C. and 3 min at 72° C. for 30 cycles, and 7 min at 72° C.

The primers used for the PCR amplification of the gag gene, from an ATG introduced into the HERV-W gag sequence on each isolated human chromosome are as follows:

```
5' primer, identified by SEQ ID NO. 14
5'-TTT GGT AAT ACG ACT CAC TAT AGG GCA GCC ACC ATG

GGA AAC GTT CCC CCC GAG-3'.
```

The primer contains the T7 RNA polymerase promoter sequence, a "spacer", the Kozak sequence (translation initiation site in eukaryotes) and the 5' gag sequence starting from the HERV-W ATG.

3' primer, identified by SEQ ID NO. 15
5'-TTTTTTTTTTTTTTTTTT
TCAGGCTGCGCCAGTGTCCAGGAGAC-3'.

The primer contains a poly-A tail (in order to stabilize the transcription of the RNA, represented by 18 T bases), a stop codon (represented by TCA) and the sequence of the MSRV-1 protease gene (G+E+A).

For the amplification of the HERV-W gag gene using oligonucleotides defined in the LTR and protease regions of HERV-W, with the Taq polymerase enzyme (Perkin Elmer, France), the PCR conditions were as follows: 3 min at 94° C.; then 1 min at 94° C., 1 min at 60° C. and 2 min at 72° C., 35 cycles; followed by 7 min at 72° C., with 50 ng of each monochromosomal DNA.

The primers used for the PCR amplification of the gag gene using the oligonucleotide defined in the HERV-W LTR sequence, on each isolated human chromosome, are as follows:

```
5' primer, identified by SEQ ID NO. 16
5'-TGTCCGCTGTGCTCCTGATC-3'

3' primer, identified by SEQ ID NO. 17
5'-TTTTTTTTTTTTTTTTTTTCAGGCTGCGCCAGTGTCCAGGAGAC-3'.
```

The primer contains a poly-A tail (in order to stabilize transcription of the RNA, represented by 18 T bases), a stop codon (represented by TCA) and the sequence of the MSRV-1 G+E+A protease gene.

The PCR amplifications were carried out in an MJ Research PTC200 Peltier Thermal cycler machine. The PCR products (10 μl of each PCR product) were analyzed in a gel of 1% agarose in 1×TBE (Tris-HCl, borate, EDTA). In order to verify the specificity of the amplification products, 3 μl of each PCR product were analyzed in agarose gel and then transferred onto a nylon membrane (Hybond® -N+, Amersham) (Southern blot) using 0.4 N NaOH. The hybridization with the gag c12 probe (1056 bp) (J. Sambrook et al., 1989) was carried out under the following conditions: after prehybridization for 4 hours (in 5×SSC, 1× Denhardt's, 0.1% SDS, 50% formamide, 20 mM Tris-HCl, pH=7.5, and 0.1 mg/ml of herring sperm DNA), the nylon membrane was hybridized (in 5×SSC, 1× Denhardt's, 0.1% SDS, 50% formamide, 20 mM Tris-HCl, pH=7.5, 0.1 mg/ml of herring sperm DNA and 5% dextran sulfate), for 18 hours at 42° C. with the $^{32}$P-labeled gag DNA probe. The gag PCR products from each isolated human chromosome were washed once, for 15 min at room temperature, in a solution of 2×SSC, 0.2% SDS; twice, for 15 min each wash at 65° C., in a solution of 0.2×SSC, 0.1% SDS; twice, for 15 min each at 65° C., in a solution of 0.1×SSC, 0.1% SDS; and twice, for 30 min each at room temperature, in a solution of 0.1×SSC, 0.1% SDS.

Part of the remaining volume (4 μl) of the PCR amplification products was used for the PTT "in vitro" transcription/translation test (Roest PAM et al., 1993) (Promega, France). The remaining volume was used for the cloning in the pCR® 2.1-TOPO vector (Invitrogen) in accordance with the instructions with the kit, and for the sequencing with the method recommended for using the "PRISM™ Ready Reaction Amplitaq® FS, DyeDeoxy™ Terminator" sequencing kit (Applied Biosystems, ref. 402119), and the automatic sequencing was carried out on Applied Biosystems 373A and 377 machines, according to the manufacturer's instructions.

By this process a 2009 bp fragment (SEQ ID NO: 2) was sequenced. The 1089 bp coding portion of the 2009 bp fragment (fragment 434-1522 of SEQ ID NO: 2), which encodes the protein of SEQ ID NO: 31, was amplified by PCR with the Pwo enzyme (5 U/μl) (Boehringer Manneim, France) using 1 μl of the minipreparation of the gag clone DNA (SEQ ID NO. 3) under the following conditions: 95° C. 1 min, 60° C. 1 min and 72° C. 2 min for 25 cycles, with a final reaction volume of 50 μl, using the primers:

–5' primer (Bam HI) (SEQ ID NO: 8):

5' ATG GGA AAC GTT CCC CCC GAG 3' (21 mer), and

–3' primer (Hind III), identified by SEQ ID NO: 9:

5' GGC CTA AGG CAG ACT TTT GAA 3' (21 mer).

The fragment obtained after PCR was linearized with Bam HI and Hind III and subcloned into the pET28C. and pET21C. expression vectors (NOVAGEN) linearized with Bam HI and Hind III. The DNA of the 1089 bp fragment in the two expression vectors were sequenced according to the method recommended for using the "PRISM™ Ready Reaction Amplitaq® FS, DyeDeoxy™ Terminator" sequencing kit (Applied Biosystems, ref. 402119) and the automatic sequencing was carried out on Applied Biosystems 373A and 377 machines, according to the manufacturer's instructions.

The expression of the nucleotide sequence of the 1089 bp fragment of the gag clone by the pET28C. and pET21C. expression vectors is identified by SEQ ID NO. 10 and SEQ ID NO. 11, respectively.

2.2—"In vitro" Transcription/Translation Test (PTT, Promega)

This test was carried out in order to pinpoint the human chromosomes which have open reading frames for the gag gene of the HERV-W family.

A mixture containing 12.5 μl of TNT® rabbit reticulocyte lysate (Promega), 1 μl of TNT® reaction buffer (Promega), 0.5 μl of TNT® RNA polymerase (Promega), 0.5 μ of a 1 mM mixture of amino acids minus methionine, 2 μl of $^{35}$S-methionine (1000 Ci/mmol) at 10 mCi/μl (Amersham), 0.5 μl of Rnasin® ribonuclease inhibitor at 40 U/μl, 4 μl of PCR amplification products (equivalent to 1 μg) from each human chromosome and 4 μl of water, in a reaction volume of 25 μl. This mixture was incubated at 30° C. for 90 min.

The gag proteins corresponding to the products of transcription/translation of the gag gene of the HERV-W family from each human chromosome, amplified by PCR, were revealed by 10% polyacrylamide gel electrophoresis in the presence of sodium dodecyl sulfate (SDS)-PAGE after exposure of the gel to the X-ray film at room temperature in the presence of an amplifying screen.

The results are given in Table 2 hereinafter.

In this table, the number indicated under each chromosome corresponds to the molecular mass (kDa) of the proteins visualized in polyacrylamide gel in the presence of SDS.

TABLE 2

| Chromo No. Rodent parent PCR gag | Chromo No. Rodent parent gag | 1 | 2 | 3 | 4 | 5 | 6 | 7 | 8 | 9 | 10 | 11 | 12 | 13 | 14 | 15 | 16 | 17 | 18 | 19 | 20 | 21 | 22 | X | Y | Water |
|---|---|---|---|---|---|---|---|---|---|---|---|---|---|---|---|---|---|---|---|---|---|---|---|---|---|---|
| | | m | h | h | h | h | h | h | h | h | h | h | h | h | h | h | m | m | h | h | m | m | h | h | h |
| | | 28 | | 45 | | | 23 | 22 | | | | | | | | | 14 | | | | | | | | | |
| | | 23 | | 25 | | | 18 | | | | | | | | | | | | | | | | | | | |
| | | 18 | | 20 | | | 17 | | | | | | | | | | | | | | | | | | | |
| | | | | 17 | | | | | | | | | | | | | | | | | | | | | | |

EXAMPLE 3

Expression of the gag Clone in *Escherichia coli*, and Reaction with Human Sera

The coding region of SEQ ID NO. 2 was expressed in *Escherichia coli*, and then the products thus expressed were tested against serum from patients suffering from MS, and also against serum from healthy patients.

The constructs pET28c-gag clone (1089 bp) and pET21C-gag clone (1089 bp) synthesize, in the BL21 (DE3) bacterial strain, an N-terminal and C-terminal fusion protein for the pET28C. vector, and a C-terminal fusion protein for the pET21C. vector, with 6 histidine residues and an apparent molecular mass of approximately 45 kDa, which are revealed by SDS-PAGE polyacrylamide gel electrophoresis (U. K. Laemmli, Cleavage of structural proteins during the assembly of the head of bacteriophage T4, Nature, 1970, 227: 680-685).

The reactivity of the protein with respect to an anti-histidine monoclonal antibody (DIANOVA) was demonstrated using the Western blot technique (H. Towbin et al., Electrophoretic transfer of proteins from polyacrylamide gels to nitrocellulose sheets: procedure and some applications, Proc. Natl. Acad. Sci. USA, 1979, 76: 4350-4354).

The recombinant proteins pET28C-gag clone (1089 bp) and pET21C-gag clone (1089 bp) were visualized, by SDS-PAGE, in the insoluble fraction after enzymatic digestion of the bacterial extracts with 50 µl of lysozyme (10 mg/ml) and lysis by ultrasound.

The antigenic properties of the recombinant antigens pET28C-gag clone (1089 bp) and pET21C-gag clone (1089 bp) were tested by Western blot after solubilization of the bacterial pellet with 2% SDS and 50 mM β-mercaptoethanol. After incubation with the sera from patients suffering from multiple sclerosis, the sera from the neurological controls and the blood transfusion center (BTC) control sera, the immunocomplexes were detected using an alkaline phosphatase-coupled anti-human IgG and IgM goat serum.

The results are given in Table 3 hereinafter.

TABLE 3

Reactivity of sera from patients suffering from multiple sclerosis and controls, with the recombinant gag protein produced in *E. coli*[a]

| DISEASE | NUMBER OF INDIVIDUALS TESTED | NUMBER OF POSITIVE INDIVIDUALS |
|---|---|---|
| MS | 15 | 6 |
| | | 2 (+++), 2 (++), 2 (+) |
| NEUROLOGICAL CONTROLS | 2 | 1 (+++) |
| HEALTHY CONTROLS (BTC) | 22 | 1 (+/−) |

(a) The strips containing 1.5 µg of recombinant gag antigen show reactivity against sera diluted 100-fold. The Western blot interpretation is based on the presence or absence of a gag-specific band on the strips. Positive and negative controls are included in each experiment.

These results show that, under the technical conditions used, approximately 40% of the human multiple sclerosis sera tested react with the recombinant gag protein.

What is claimed is:

1. An isolated nucleic acid molecule consisting of:
a sequence belonging to a gag gene of an endogenous retrovirus selected from the group consisting of:
(i) the sequence consisting of SEQ ID NO:2;
(ii) a sequence consisting of an open reading frame encoding a polypeptide, wherein the polypeptide encoded in the open reading frame consists of SEQ ID NO:31; and
(iii) the sequence that is fully complementary to sequence (i) or (ii).

2. An isolated transcription product selected from the group consisting of:

(i) the sequence consisting of SEQ ID NO:2; and
(ii) a sequence consisting of an open reading frame encoding a polypeptide, wherein the polypeptide encoded in the open reading frame consists of SEQ ID NO:31.

3. A reagent comprising at least one isolated nucleic acid molecule according to claim 1.

4. A reagent comprising at least one transcription product according to claim 2.

5. The nucleic acid molecule according to claim 1, wherein said molecule consists of the sequence set forth in SEQ ID NO:2.

* * * * *

SEQUENCE LISTING

<160> NUMBER OF SEQ ID NOS: 33

<210> SEQ ID NO 1
<211> LENGTH: 1511
<212> TYPE: DNA
<213> ORGANISM: Homo sapiens

<400> SEQUENCE: 1

```
cctagaacgt attctggaga attgggacca atgtgacact cagacgctaa gaaagaaacg      60
atttatattc ttctgcagta ccgcctggcc acaatatcct cttcaaggga gagaaacctg     120
gcttcctgag ggaagtataa attataacat catcttacag ctagacctct tctgtagaaa     180
ggagggcaaa tggagtgaag tgccatatgt gcaaactttc tttcattaa gagacaactc      240 acaattatgt aaaaagtgtg gtttatgccc tacaggaagc cctcagagtc cacctcccta     300
ccccagcgtc ccctccccga ctccttcctc aactaataag gacccccctt taacccaaac     360
ggtccaaaag gagatagaca aaggggtaaa caatgaacca aagagtgcca atattcccg      420
```

-continued

```
attatgcccc ctccaagcag tgagaggagg agaattcggc ccagccagag tgcctgtacc      480
tttttctctc tcagacttaa agcaaattaa aatagaccta ggtaaattct cagataaccc      540
tgacggctat attgatgttt tacaagggtt aggacaatcc tttgatctga catggagaga      600
tataatgtta ctactaaatc agacactaac cccaaatgag agaagtgccg ctgtaactgc      660
agcccgagag tttggcgatc tttggtatct cagtcaggcc aacaatagga tgacaacaga      720
ggaaagaaca actcccacag gccagcaggc agttcccagt gtagaccctc attgggacac      780
agaatcagaa catggagatt ggtgccacaa acatttgcta acttgcgtgc tagaaggact      840
gaggaaaact aggaagaagc ctatgaatta ctcaatgatg tccactataa cacagggaaa      900
ggaagaaaat cttactgctt ttctggacag actaagggag gcattgagga agcatacctc      960
cctgtcacct gactctattg aaggccaact aatcttaaag gataagttta tcactcagtc     1020
agctgcagac attagaaaaa acttcaaaag tctgccttag gcccggagca gaacttagaa     1080
accctattta acttggcatc ctcagttttt tataatagag atcaggagga gcaggcgaaa     1140
cgggacaaac gggataaaaa aaaaggggg ggtccactac tttagtcatg gccctcaggc     1200
aagcagactt tggaggctct gcaaaaggga aagctgggc aaatcaaatg cctaataggg     1260
ctggcttcca gtgcggtcta caaggacact ttaaaaaaga ttatccaagt agaaataagc     1320 cgccccttg tccatgcccc ttacgtcaag ggaatcactg gaaggccac tgccccaggg     1380 gatgaagata ctctgagtca gaagccatta accagatgat ccagcagcag gactgagggt     1440
gcccggggcg agcgccagcc catgccatca ccctcacaga gccccgggta tgtttgacca     1500
ttgagagcca a                                                          1511
```

<210> SEQ ID NO 2
<211> LENGTH: 2009
<212> TYPE: DNA
<213> ORGANISM: Homo sapiens
<220> FEATURE:
<221> NAME/KEY: misc_feature
<222> LOCATION: (1940)..(1940)
<223> OTHER INFORMATION: n = a or g or c or t/u

<400> SEQUENCE: 2

```
atacgactac tatagggcga attgggccct ctagatgcat gctcgagcgg ccgccagtgt       60
gatggatatc tgcagaattc gcccttgtc cgctgtgctc ctgatccagc gaggcgccca      120
ttgctgctcc caattgggct aaaggcttgc cattgttccc acacggctaa gtgcccgggt      180
tcatcctaat tgagctgaac actagtcact gggttccatg gttctcttcc atgacccacg      240
gcttctaata gagctctaat actcaccaca tggcccaaga ttccattcct tggaatccgt      300
gaggccaaga accccaggtc agagaacacg aggcttgcca ccgtcttgga agtggcccgc      360
cgccatcttg ggagctctgg gagcaaggac ccccccagtaa catttggca accacaaagg     420 gacctccaaa gcgatgggaa acattccccc caaggcaaaa acgcccctaa gatgtattct      480
ggagaattgg gaccaatgtg acactcagac gctaagaaag aaacgattta tattcttctg      540
cagtaccgcc tggccacaat atcctcttca agggagagaa acctggcttc ctgagggaag      600
tataaattat aacatcatct tacagctaga cctcttctgt agaaaggagg gcaaatggag      660
tgaagtgcca tatgtgcaaa cttttcttttc attaagagac aactcacaat tatgtaaaaa      720
gtgtggttta tgcctacag gaagccctca gagtccacct ccctacccca gcgtcccccc      780
cccgactcct tcctcaacta ataaggaccc ccctttaacc caaacggtcc aaaaggagat      840
```

| | | |
|---|---|---|
| agacaaaggg gtaaacaatg aaccaaagag tgccaatatt ccccgattat gcccctcca | 900 |
| agcagtgaga ggaggagaat tcggcccagc cagagtgcct gtaccttttt ctctctcaga | 960 |
| cttaaagcaa attaaaatag acctaggtaa attctcagat aaccctgacg gctatattga | 1020 |
| tgttttacaa gggttaggac aatcctttga tctgacatgg agagatataa tgttactact | 1080 |
| aaatcagaca ctaaccccaa atgagagaag tgccgctgta actgcagccc gagagtttgg | 1140 |
| cgatctttgg tatctcagtc aggtcaacaa taggatgaca acagaggaaa gaacaactcc | 1200 |
| cacaggccag caggcagttc ccagtgtaga ccctcattgg gacacagaat cagaacatgg | 1260 |
| agattggtgc cacaaacatt tgctaacttg cgtgctagaa ggactgagga aaactaggaa | 1320 |
| gaagcctatg aattactcaa tgatgtccac tataacacag ggaaaggaag aaaatcctac | 1380 |
| tgcttttctg gacagactaa gggaggcatt gaggaagcat acctccctgt cacctgactc | 1440 |
| tattgaaggc caactaatct taaggataa gtttatcact cagtcagctg cagacattag | 1500 |
| aaaaaacttc aaaagtctgc cttaggcccg gagcagaact tagaaaccct atttaacttg | 1560 |
| gcatcctcag ttttttataa tagagatcag gaggagcagg cgaaacggga caaacgggat | 1620 |
| aaaaaaaaaa gggggggtcc actactttag tcatggccct caggcaagca gactttggag | 1680 |
| gctctggaaa agggaaaagc tgggcaaatc aaatgcctaa tagggctggc ttccagtgcg | 1740 |
| gtctacaagg acactttaaa aaagattatc caagtagaaa taagccgccc ccttgtccat | 1800 |
| gccccttacg tcaagggaat cactggaagg cccactgccc caggggatga agatactctg | 1860 |
| agtcagaagc cattaaccag atgatccagc agcaggactg agggtgcccg gggcgagcgc | 1920 |
| cagcccatgc catcaccctn acagagcccc gggtatgctt gaccattgag agccaggagg | 1980 |
| ttaactgtct cctggacact ggcgcagcc | 2009 |

<210> SEQ ID NO 3
<211> LENGTH: 1056
<212> TYPE: DNA
<213> ORGANISM: Homo sapiens

<400> SEQUENCE: 3

| | | |
|---|---|---|
| ctagaacgta ttctggagaa ttgggaccaa tgtgacactc agacgctaag aaagaaacga | 60 |
| tttatattct tctgcagtac cgcctggcca caatatcctc ttcaagggag agaaacctgg | 120 |
| cttcctgagg gaagtataaa ttataacatc atcttacagc tagacctctt ctgtagaaag | 180 |
| gagggcaaat ggagtgaagt gccatatgtg caaactttct tttcattaag agacaactca | 240 |
| caattatgta aaaagtgtgg tttatgccct acaggaagcc ctcagagtcc acctccctac | 300 |
| cccagcgtcc cctccccgac tccttcctca actaataagg acccccttt aacccaaacg | 360 |
| gtccaaaagg agatagacaa agggtaaac aatgaaccaa agagtgccaa tattccccga | 420 |
| ttatgccccc tccaagcagt gagaggagga gaattcggcc cagccagagt gcctgtacct | 480 |
| ttttctctct cagacttaaa gcaaattaaa atagacctag gtaaattctc agataaccct | 540 |
| gacggctata ttgatgtttt acaagggtta ggacaatcct ttgatctgac atggagagat | 600 |
| ataatgttac tactaaatca gacactaacc ccaaatgaga gaagtgccgc tgtaactgca | 660 |
| gcccgagagt ttggcgatct ttggtatctc agtcaggcca acaataggat gacaacagag | 720 |
| gaaagaacaa ctcccacagg ccagcaggca gttcccagtg tagaccctca ttgggacaca | 780 |
| gaatcagaac atggagattg gtgccacaaa catttgctaa cttgcgtgct agaaggactg | 840 |
| aggaaaacta ggaagaagcc tatgaattac tcaatgatgt ccactataac acagggaaag | 900 |
| gaagaaaatc ttactgcttt tctggacaga ctaagggagg cattgaggaa gcatacctcc | 960 |

```
ctgtcacctg actctattga aggccaacta atcttaaagg ataagtttat cactcagtca    1020
gctgcagaca ttagaaaaaa cttcaaaagt ctgcct                              1056
```

<210> SEQ ID NO 4
<211> LENGTH: 25
<212> TYPE: DNA
<213> ORGANISM: Homo sapiens

<400> SEQUENCE: 4

```
cggacatcca aagtgatggg aaacg                                          25
```

<210> SEQ ID NO 5
<211> LENGTH: 26
<212> TYPE: DNA
<213> ORGANISM: Homo sapiens

<400> SEQUENCE: 5

```
ggacaggaaa gtaagactga aaggc                                          26
```

<210> SEQ ID NO 6
<211> LENGTH: 26
<212> TYPE: DNA
<213> ORGANISM: Homo sapiens

<400> SEQUENCE: 6

```
cctagaacgt attctggaga attggg                                         26
```

<210> SEQ ID NO 7
<211> LENGTH: 26
<212> TYPE: DNA
<213> ORGANISM: Homo sapiens

<400> SEQUENCE: 7

```
tggctctcaa tggtcaaaca tacccg                                         26
```

<210> SEQ ID NO 8
<211> LENGTH: 21
<212> TYPE: DNA
<213> ORGANISM: Homo sapiens

<400> SEQUENCE: 8

```
atgggaaacg ttccccccga g                                              21
```

<210> SEQ ID NO 9
<211> LENGTH: 21
<212> TYPE: DNA
<213> ORGANISM: Homo sapiens

<400> SEQUENCE: 9

```
ggcctaaggc agactttga a                                               21
```

<210> SEQ ID NO 10
<211> LENGTH: 409
<212> TYPE: PRT
<213> ORGANISM: Homo sapiens

<400> SEQUENCE: 10

```
Met Gly Ser Ser His His His His His His Ser Ser Gly Leu Val Pro
1               5                   10                  15

Arg Gly Ser His Met Ala Ser Met Thr Gly Gly Gln Gln Met Gly Arg
            20                  25                  30
```

```
Ile Met Gly Asn Ile Pro Pro Lys Ala Lys Thr Pro Leu Arg Cys Ile
            35                  40                  45

Leu Glu Asn Trp Asp Gln Cys Asp Thr Gln Thr Leu Arg Lys Lys Arg
 50                  55                  60

Phe Ile Phe Phe Cys Ser Thr Ala Trp Pro Gln Tyr Pro Leu Gln Gly
 65                  70                  75                  80

Arg Glu Thr Trp Leu Pro Glu Gly Ser Ile Asn Tyr Asn Ile Ile Leu
                85                  90                  95

Gln Leu Asp Leu Phe Cys Arg Lys Glu Gly Lys Trp Ser Glu Val Pro
            100                 105                 110

Tyr Val Gln Thr Phe Phe Ser Leu Arg Asp Asn Ser Gln Leu Cys Lys
            115                 120                 125

Lys Cys Gly Leu Cys Pro Thr Gly Ser Pro Gln Ser Pro Pro Pro Tyr
        130                 135                 140

Pro Ser Val Pro Pro Thr Pro Ser Ser Thr Asn Lys Asp Pro Pro
145                 150                 155                 160

Leu Thr Gln Thr Val Gln Lys Glu Ile Asp Lys Gly Val Asn Asn Glu
                165                 170                 175

Pro Lys Ser Ala Asn Ile Pro Arg Leu Cys Pro Leu Gln Ala Val Arg
            180                 185                 190

Gly Gly Glu Phe Gly Pro Ala Arg Val Pro Val Pro Phe Ser Leu Ser
        195                 200                 205

Asp Leu Lys Gln Ile Lys Ile Asp Leu Gly Lys Phe Ser Asp Asn Pro
210                 215                 220

Asp Gly Tyr Ile Asp Val Leu Gln Gly Leu Gly Gln Ser Phe Asp Leu
225                 230                 235                 240

Thr Trp Arg Asp Ile Met Leu Leu Leu Asn Gln Thr Leu Thr Pro Asn
                245                 250                 255

Glu Arg Ser Ala Ala Val Thr Ala Ala Arg Glu Phe Gly Asp Leu Trp
            260                 265                 270

Tyr Leu Ser Gln Val Asn Asn Arg Met Thr Thr Glu Glu Arg Thr Thr
        275                 280                 285

Pro Thr Gly Gln Gln Ala Val Pro Ser Val Asp Pro His Trp Asp Thr
290                 295                 300

Glu Ser Glu His Gly Asp Trp Cys His Lys His Leu Leu Thr Cys Val
305                 310                 315                 320

Leu Glu Gly Leu Arg Lys Thr Arg Lys Lys Pro Met Asn Tyr Ser Met
                325                 330                 335

Met Ser Thr Ile Thr Gln Gly Lys Glu Glu Asn Pro Thr Ala Phe Leu
            340                 345                 350

Asp Arg Leu Arg Glu Ala Leu Arg Lys His Thr Ser Leu Ser Pro Asp
        355                 360                 365

Ser Ile Glu Gly Gln Leu Ile Leu Lys Asp Lys Phe Ile Thr Gln Ser
    370                 375                 380

Ala Ala Asp Ile Arg Lys Asn Phe Lys Ser Leu Pro Lys Leu Ala Ala
385                 390                 395                 400

Ala Leu Glu His His His His His His
                405
```

<210> SEQ ID NO 11
<211> LENGTH: 393
<212> TYPE: PRT
<213> ORGANISM: Homo sapiens

<400> SEQUENCE: 11

```
Met Ala Ser Met Thr Gly Gly Gln Gln Met Gly Arg Ile Met Gly Asn
1               5                   10                  15

Ile Pro Pro Lys Ala Lys Thr Pro Leu Arg Cys Ile Leu Glu Arg Ile
                20                  25                  30

Leu Glu Asn Trp Asp Gln Cys Asp Thr Gln Thr Leu Arg Lys Lys Arg
            35                  40                  45

Phe Ile Phe Phe Cys Ser Thr Ala Trp Pro Gln Tyr Pro Leu Gln Gly
50                  55                  60

Arg Glu Thr Trp Leu Pro Glu Gly Ser Ile Asn Tyr Asn Ile Ile Leu
65                  70                  75                  80

Gln Leu Asp Leu Phe Cys Arg Lys Glu Gly Lys Trp Ser Glu Val Pro
                85                  90                  95

Tyr Val Gln Thr Phe Phe Ser Leu Arg Asp Asn Ser Gln Leu Cys Lys
                100                 105                 110

Lys Cys Gly Leu Cys Pro Thr Gly Ser Pro Gln Ser Pro Pro Pro Tyr
                115                 120                 125

Pro Ser Val Pro Ser Pro Thr Pro Ser Ser Thr Asn Lys Asp Pro Pro
130                 135                 140

Leu Thr Gln Thr Val Gln Lys Glu Ile Asp Lys Gly Val Asn Asn Glu
145                 150                 155                 160

Pro Lys Ser Ala Asn Ile Pro Arg Leu Cys Pro Leu Gln Ala Val Arg
                165                 170                 175

Gly Gly Glu Phe Gly Pro Ala Arg Val Pro Val Pro Phe Ser Leu Ser
                180                 185                 190

Asp Leu Lys Gln Ile Lys Ile Asp Leu Gly Lys Phe Ser Asp Asn Pro
                195                 200                 205

Asp Gly Tyr Ile Asp Val Leu Gln Gly Leu Gly Gln Ser Phe Asp Leu
                210                 215                 220

Thr Trp Arg Asp Ile Met Leu Leu Leu Asn Gln Thr Leu Thr Pro Asn
225                 230                 235                 240

Glu Arg Ser Ala Ala Val Thr Ala Ala Arg Glu Phe Gly Asp Leu Trp
                245                 250                 255

Tyr Leu Ser Gln Ala Asn Asn Arg Met Thr Thr Glu Glu Arg Thr Thr
                260                 265                 270

Pro Thr Gly Gln Gln Ala Val Pro Ser Val Asp Pro His Trp Asp Thr
                275                 280                 285

Glu Ser Glu His Gly Asp Trp Cys His Lys His Leu Leu Thr Cys Val
                290                 295                 300

Leu Glu Gly Leu Arg Lys Thr Arg Lys Lys Pro Met Asn Tyr Ser Met
305                 310                 315                 320

Met Ser Thr Ile Thr Gln Gly Lys Glu Glu Asn Leu Thr Ala Phe Leu
                325                 330                 335

Asp Arg Leu Arg Glu Ala Leu Arg Lys His Thr Ser Leu Ser Pro Asp
                340                 345                 350

Ser Ile Glu Gly Gln Leu Ile Leu Lys Asp Lys Phe Ile Thr Gln Ser
                355                 360                 365

Ala Ala Asp Ile Arg Lys Asn Phe Lys Ser Leu Pro Lys Leu Ala Ala
                370                 375                 380

Ala Leu Glu His His His His His His
385                 390
```

<210> SEQ ID NO 12
<211> LENGTH: 26

```
<212> TYPE: DNA
<213> ORGANISM: Homo sapiens

<400> SEQUENCE: 12
ctagaacgta ttctggagaa ttggga                                          26

<210> SEQ ID NO 13
<211> LENGTH: 20
<212> TYPE: DNA
<213> ORGANISM: Homo sapiens

<400> SEQUENCE: 13
cctaaggcag acttttgaag                                                 20

<210> SEQ ID NO 14
<211> LENGTH: 54
<212> TYPE: DNA
<213> ORGANISM: Homo sapiens

<400> SEQUENCE: 14
tttggtaata cgactcacta tagggcagcc accatgggaa acgttccccc cgag           54

<210> SEQ ID NO 15
<211> LENGTH: 44
<212> TYPE: DNA
<213> ORGANISM: Homo sapiens

<400> SEQUENCE: 15
tttttttttt tttttttttc aggctgcgcc agtgtccagg agac                      44

<210> SEQ ID NO 16
<211> LENGTH: 20
<212> TYPE: DNA
<213> ORGANISM: Homo sapiens

<400> SEQUENCE: 16
tgtccgctgt gctcctgatc                                                 20

<210> SEQ ID NO 17
<211> LENGTH: 44
<212> TYPE: DNA
<213> ORGANISM: Homo sapiens

<400> SEQUENCE: 17
tttttttttt tttttttttc aggctgcgcc agtgtccagg agac                      44

<210> SEQ ID NO 18
<211> LENGTH: 678
<212> TYPE: DNA
<213> ORGANISM: Homo sapiens
<220> FEATURE:
<221> NAME/KEY: misc_feature
<222> LOCATION: (594)..(594)
<223> OTHER INFORMATION: n = a or g or c or t/u

<400> SEQUENCE: 18
tcagggatag cccccatcta tttggccagg cattagccca agacttgagc cagttctcat     60
acctggatat tcttgtcctt tggtatgcgg atgatttact tttagccgcc cgttcagaaa   120
ccttgtgcca tcaagccacc caagtgctct taaatttcct cgccacctgt ggctacaagg   180
tttccaaacc aaaggctcag ctctgctcac agcagaaggc tatttaccct aaatacttag   240
ggctgaaatt atccaaaggc accagggccc tcagtgagga atgtatccag cctatactgg   300
```

```
cttatcctta tcccaaaacc ctaaaacaac taagaaggtt ccttggcata ataggcataa      360
caggcataac aggtttctgc tgaatatgga ttcccaagta cggcaaaata gccagaccat      420
tatatacact aattaaggaa actcagaaag ccaataccca tttagtaaga tggacacctg      480
aagcagaggc agctttccag gccgtaaaga cacccctaac ccaagcccca gtgttaagct      540
tgccagcggg gcaagacttt tctttctgtg tcacagaaaa aataggaata gctntaggag      600
tccttacaca ggtccgaggg accagcttgc aacccatggc atacctgagt aaggaaattg      660
atgtagtggc aaagggtt                                                   678
```

`<210>` SEQ ID NO 19
`<211>` LENGTH: 591
`<212>` TYPE: DNA
`<213>` ORGANISM: Homo sapiens

`<400>` SEQUENCE: 19

```
ccatggccat ctacactgaa caagatttat acaatcatgt cgtacctaag ccccacaaca       60
aaagagtacc cattcttcct tttgttatca gagcaggagt gctaggcaga ctaggtactg      120
gcattggcag tatcacaacc tctactcagt tctactacaa actatctcaa gaatataaatg     180 gtgacatgga acaggtcact gactccctgg tcaccttgca agatcaactt aactccctag      240
cagcagtagt ccttcaaaat cgaagagctt tagacttgct aaccgccaaa agaggggaa       300 cctgtttatt tttaggagaa gaacgctgtt attatgttaa tcaatccaga attgtcactg      360
agaaagttaa agaaattcga gatcgaatac aatgtagagc agaggagctt caaaacaccg      420
aacgctgggg cctcctcagc caatggatgc cctgggttct cccctccta ggacctctag       480 cagctctaat attgttactc ctctttggac cctgtatctt taacctcctt gttaagtttg      540
tctcttccag aattgaagct gtaaagctac agatggtctt acaaatctag a              591
```

`<210>` SEQ ID NO 20
`<211>` LENGTH: 1321
`<212>` TYPE: DNA
`<213>` ORGANISM: Homo sapiens

`<400>` SEQUENCE: 20

```
caacaatcgg gatataaacc caggcattcg agctggcaac agcagccccc ctttgggtcc       60
cttccctttg tatgggagct gttttcatgc tatttcactc tattaaatct tgcaactgca      120
ctcttctggt ccatgtttct tacggctcga gctgagcttt tgctcaccgt ccaccactgc      180
tgtttgccac caccgcagac ctgccgctga ctcccatccc tctggatcct gcagggtgtc      240
cgctgtgctc ctgatccagc gaagcgccca ttgccgctcc caattgggct aaaggcttgc      300
cattgttcct gcacggctaa gtgcctgggt ttgttctaat tgagctgaac actagtcact      360
gggttccatg gttctcttct gtgacccacg gcttctaata gaactataac acttaccaca      420
tggcccaaga ttccattcct tggaatccgt gaggccaaga actccaggtc agagaatacg      480
aagcttgcca ccatcttgga agcggcctgc taccatcttg aagtggttc accaccatct       540 tgggagctct gtgagcaagg acccccccggt aacattttgg caaccacgaa cggacatcca     600
aagtgatggg aaacgttccc cgcaagacaa aaacgcccct aagacgtatt ctggaaaatt      660
gggaacaatt tgaccctcag acactaagaa agaaacgact tatattcttc tgcagtgccg      720
cctggcactc ctgagggaag tataaattat aacaccatct tacagctaga cctcttttgt      780
agaaaaggca aatggagtga agtgccataa gtacaaactt cttttcatt aagagacaac       840 tcacaattat gtaaaagtg tgatttatgc cctacaggaa gccttcagag tctacctccc        900
```

```
tatcccagca tccccgactc cttccccact taataaggac cccccttcaa cccaaatggt        960
ccaaaaggag atagacaaaa gggtaaacag tgaaccaaag agtgccaata ttccccaatt       1020
atgacccctc caagcagtgg gaggaagaga attcggccca gccagagtgc atgtgccttt       1080
ttctctccca gacttaaagc aaataaaaac agacttaggt aaattctcag ataaccctga       1140
tggctatatt ggtgttttac aagggttagg acaattcttt gatctgacat ggagagatat       1200
atatgtcact gctaaatcag acactaaccc caaatgagag aagtgccacc ataactgcag       1260
cctgagagtt tggcgatctc tggtatctca gtcaggtcaa tgataggatg acaacagagg       1320
a                                                                      1321
```

<210> SEQ ID NO 21
<211> LENGTH: 2938
<212> TYPE: DNA
<213> ORGANISM: Homo sapiens

<400> SEQUENCE: 21

```
caacgacgga catccaaagt gatgggaaac gttcccgca agacaaaaac gcccctaaga         60
cgtattctgg agaattggga ccaatttgac cctcagacac taagaaagaa acgacttata        120
ttcttctgca gtgccgcctg gcactcctga gggaagtata aattataaca ccatcttaca        180
gctagacttc ttttgtagaa aaggcaaatg gagtgaagtg ccataagtac aaactttctt        240
ttcattaaga gacaactcac aattatgtaa aaagtgtgat ttatgcccta caggaagcct        300
tcagagtcta cctccctatc ccagcatccc cgactccttc cccaactaat aaggaccccc        360
cttcaaccca aatggtccaa aaggagatag acaaagggt aaacagtgaa ccaaagagtg         420
ccaatattcc ccaattatga cccctcccaa gcagtgggag gaagagattc ggcccagcca        480
gagtgcatgt gctttttctt ctcccagact taaagcaaat aaaaacagac ttaggtaaat        540
tctcagataa tcctgatggc tatattgatg ttttacaagg gttaggacaa ttctttgatc        600
tgacatggag agatataatg tcactgctaa atcagacact aaccccaaat gagagaagtg        660
ccaccataac tgcagcctga gagtttggcg atctctggta tctcagtcag gtcaatgata        720
ggatgacaac agaggaaaga gatgatcccc acagccagca agcagttccc agtctasacc        780
ctcattgggg acacagaaat cagtaacatg ggagattggt gctgcagaca tttgctaact        840
tgtgtgctac aaggactaag gaaaactacg aagaaatct acgaattact caatgatgtc         900
caccataaca caggggaagg gaagaaaatc tactgccctt tctggagaga ctaagggagg        960
cattgaggaa gcgtgcctct ctgtcacctg actcttctga aggccaacta atcttaaagc       1020
gtaagtttat cactcagtca gctgcagaca ttagaaaaaa cttcaaaagt ctgccgtagg       1080
cccggagcaa aacttagaaa ccctattgaa cttggcaacy tcggtttttt ataatagaga       1140
tcaggaggag caggcggaac aggacaaacg ggattaaaaa aaaggccacc gctttagtca       1200
tgaccctcag gcaagtggac tttggaggct ctggaaaagg gaaaagctgg gcaaattgaa       1260
tgcctaatag ggcttgcttc cagtgcggtc tacaaggaca ctttaaaaaa gattgtccaa       1320
gtagaagtaa gccgcccctt cgtccatgcc ccttatttca agggaatcac tggaaggccc       1380
actgccccag gggacaaagg tcttttgagt cagaagccac taaccagatg atccagcagc       1440
aggactgagg gtgcctgggg caagcgccat cccatgccat caccctcaca gagccctggg       1500
tatgcttgac cattgagggc caggaaggtt gtcctctgga cactggtgcg gtcttcttag       1560
tcttactctt ctgtcccgga caactgtcct ccagatctgt cactatctga gggggtccta       1620
```

```
agacgggcag tcactagata cttctcccag ccactaagtt atgactgggg agctttattc      1680
ttttcacatg cttttctaat tatgcttgaa agccccacta ccttgttagg gagagacatt      1740
ctagcaaaag cagggccat tatacacctg aacataggag aaggaacacc cgtttgttgt       1800
cccctgcttg aggaaggaat taatcctgaa gtctgggcaa cagaaggaca atatggacga      1860
gcaaagaatg cccgtcctgt tcaagttaaa ctaaaggatt ccacttcctt tccctaccaa      1920
aggcagtacc ccctcagacc caaggcccaa caaggattcc aaaagattgt taaggactta     1980
aaagcccaag gcttagtaaa accatgcata actccctgca gtaattccgt agtggattga      2040
ggaggcacag aaacccagtg gacagtggag ggttagtgca agatctcagg attatcaatg     2100
gaggccgttg tccttttata cccagctgta cctagccctt atactgtgct ttcccaaata     2160
ccagaggaag cagagtggtt tacactcctg gaccttaagg atgccttctt ctgcatccct      2220
gtacatcctg actctcaatt cttgtttgcc tttgaagata cttcaaaccc aacatctcaa     2280
ctcacctgga ctgttttacc ccaagggttc agggatagcc cccatctatt tggccaggca     2340
ttagcccaag acttgagcca atcctcatac ctggacactt gtccttcggt aggtggatga     2400
tttacttttg gccgcccatt cagaaacctt gtgccatcaa gccacccaag cgctcttcaa     2460
tttcctcgct acctgtggct acatggtttc caaaccaaag gctcaactct gctcacagca     2520
ggttacttag ggctaaaatt atccaaaggc accagggccc tcagtgagga acacatccag      2580
cctatactgg cttatcctca tcccaaaacc ctaaagcaac taaggggatt ccttggcgta     2640 ataggttttct gccgaaaatg gattcccagg tttggcgaaa tagccaggtc attaaataca    2700
ctaattaagg aaactcagaa agccaatacc catttagtaa gatggacaac tgaagtagaa    2760
gtggctttcc aggccctaac ccaagcccca gtgttaagtt tgccaacagg gcaagacttt     2820
tcttcatatg tcacagaaaa aacaggaata gctctaggag tccttacaca gatccgaggg      2880
atgagcttgc aacctgtggc gtacctgact aaggaaattg atgtagtggc aaagggtt      2938
```

```
<210> SEQ ID NO 22
<211> LENGTH: 1422
<212> TYPE: DNA
<213> ORGANISM: Homo sapiens
<220> FEATURE:
<221> NAME/KEY: misc_feature
<222> LOCATION: (879)..(879)
<223> OTHER INFORMATION: n = a or g or c or t/u
<220> FEATURE:
<221> NAME/KEY: misc_feature
<222> LOCATION: (1200)..(1200)
<223> OTHER INFORMATION: n = a or g or c or t/u

<400> SEQUENCE: 22
```

```
tcagggatag cccccatcta tttggccagg cattagccca agacttgagt cagttatcat        60
acctggacac tcttgtcctt cagtatgtgg atgatttact tttagctgcc tgttcagaaa       120
ccttgtgcca tcaagccacc caagcactct taaatttcct cgccaccgt ggctacaagg        180 tttccaaaga gaagctcagc tctgctcaca gcaggttaaa tacttaggac taagattatc       240
caaaggcacc aaggccctca gtgaggaatg tatccagcct atactggctt atcctcatct       300
caaaacccta aagcaactaa gagagttcct tggcataaca ggcttctgcc gaatatggat       360
tccccaggta tggcaaaata gccaggcat tatatacagt aattaaggaa actcagaaag       420 ccaatacca tttaataaga tggatacctg aagccaaagt ggctttccag gcccctaaag       480
aaggccttaa acccaagtcc cagtgttaag cttgccaacg gggcaagact tttcttata       540 catcacagaa aaaaacagaa acagctctgg gagtccttac acaggtccaa gggacgagct       600
```

```
tgcaacccat ggcatacctg agtaaggaaa ctgatgtagt ggcaaagggt tggcttcatt      660
gtttatgggt agtggtggca gtagcagttg tagtatctga agcagttaaa ataatacagg      720
ggagagatct tactgtgtgg acatctcatg aggtgaacag catactcact gctaaaggag      780
acttgtggct gtcagacaac cgtttactta aatatcaggc tctattactt gaaaggccag      840
tgctgcaact gtgcacttgt gcaactctta acccagtcnc atttcttcca gacaatgaag      900
atagaatata actgtcaaca ataaatttct caaacctatg ccactcgagg ggaccttcta      960
gaagttccct tgactgatcc tgaccttcaa cttgtatact gatggaagtt cctttgtaga     1020
aaaaggactt caaaagcggg gtatgcagtg gtcagtgata atggaatatt tgaaagtatc     1080
ccctcactcc aggaactagt gcttagctgg cagaactaat agccttcatt ggggcactag     1140
aattaggaga aggaaaaagg gtaaatatat atacagactc tgagtatgct cacctagtcn     1200
tccatgccca tgaggcaata tgcagagaaa gggaattcct aacttccgag gaacaccta     1260 tcacacatca ggaagccatt aggagattat tactggcagt acagaaacct aaagaggtgg     1320
aagtcttaca ctgctggggt catcagaaag gaaagaaaag ggaaatagaa gggaattgcc     1380
aagcagatat tgaagcaaaa agagctgcaa ggcaggaccc tc                        1422
```

<210> SEQ ID NO 23
<211> LENGTH: 2006
<212> TYPE: DNA
<213> ORGANISM: Homo sapiens
<220> FEATURE:
<221> NAME/KEY: misc_feature
<222> LOCATION: (305)..(305)
<223> OTHER INFORMATION: n = a or g or c or t/u

<400> SEQUENCE: 23

```
atgcagtggt cagtgataat ggaatacttg aaagtaatcc cctcactcca ggaactagtg       60
ctcagctagc agaactaata gccctcactt gggcactaga attaggagaa gaaaaaaggg     120
caaatatata tacagactct aaatatgctt acctagtcct ccatgcccat gcagcaatat      180
ggaaagaaag ggaattccta acttctgaga gaacacctat caaacatcag gaagccatta     240
ggaaattatt attggctgta cagaaaccta agaggtggc agtcttacac tgccggggtc      300
atcanaaagg aaaggaaagg gaaaatactt ttgcctgcaa ctatccaatg gaaattactt     360
aaaccccttc atcaaacctt tcacttaggc atcgatagca cccatcaaat ggccaaatca     420
ttatttactg gaccaggcct tttcaaaact atcaagcaaa tattcagggc ctgtgaattg     480
tgccaaaaaa ataatcccct gcctcatcgc caagctcctt caggaaaaca aaaaacaggc     540
cattaccctg aaaaaaactg gcaactgatt ttacccacaa gcccaaacct cagggatttc     600
agtatctact agtctgggta aatactttca cgggttgggc aaaggccttc ccctgtagga     660
cagaaaaggc ccaagaggta ataaaggcac tagttcatga ataattccc agattcggac      720 ttcccccgagg cttacagagt gacaatagcc ctgctttcca ggccacagta acccagggag     780
tatcccaggc gttaggtata cgatatcact tacactgcgc ctgaaggcca cagtcctcag     840
ggaaggtcga gaaatgaat gaaatactca aaggacatct aaaaaagcaa acccaggaaa     900
cccacctcac atggcctgct ctgttgccta tagccttaaa aagaatctgc aacttcccc     960 aaaaagcagg acttagccca tacgaaatgc tgtatggaag gccttcata accaatgacc     1020 ttgtgcttga cccaagacag ccaacttagt tgcagacatc acctccttag ccaaatatca     1080
acaagttctt aaaacattac aaggaaccta tccctgagaa gagggaaaag aactattcca     1140
```

-continued

```
cccttgtgac atggtattag tcaagtccct tctctctaat tccccatccc tagatacatc    1200
ctgggaagga ccctacccag tcattttatt taccccaact gcggttaaag tggctggagt    1260
ggtcttggat acatcacact tgagtcaaat cctggatact gccaaaggaa cctgaaaatc    1320
caggagacaa cgctagctat tcctgtgaac ctctagagga tttgcgcctg ctcttcaaac    1380
aacaaccagg aggaaagtaa ctaaaatcat aaatccccca tggccctccc ttatcatatt    1440
tttctcttta ctgttctttt accctctttc actctcactg cacccctcc atgccgctgt     1500 atgaccagta gctcccctta ccaagagttt ctatggagaa tgcagcgtcc cggaaatatt    1560
gatgccccat cgtataggag tctttctaag ggaaccccca ccttcactgc ccacaccat     1620 atgccccgca actgctatca ctctgccact ctttgcatgc atgcaaatac tcattattgg    1680
acaggaaaaa tgattaatcc tagttgtcct ggaggacttg gagtcactgt ctgttggact    1740
tacttcaccc aaactggtat gtctgatggg ggtggagttc aagatcaggc aagagaaaaa    1800
catgtaaaag aagtaatctc ccaactcacc cgggtacatg gcacctctag ccctacaaag    1860
gactagatct ctcaaaacta catgaaaccc tccgtaccca tactcgcctg gtaagcctat    1920
ttaataccac cctcactggg ctccatgagg tctcggccca aaaccctact aactgttgga    1980
tatgcctccc cctgaacttc aagcca                                        2006

<210> SEQ ID NO 24
<211> LENGTH: 1948
<212> TYPE: DNA
<213> ORGANISM: Homo sapiens
<220> FEATURE:
<221> NAME/KEY: misc_feature
<222> LOCATION: (84)..(84)
<223> OTHER INFORMATION: n = a or g or c or t/u
<220> FEATURE:
<221> NAME/KEY: misc_feature
<222> LOCATION: (193)..(193)
<223> OTHER INFORMATION: n = a or g or c or t/u
<220> FEATURE:
<221> NAME/KEY: misc_feature
<222> LOCATION: (241)..(241)
<223> OTHER INFORMATION: n = a or g or c or t/u

<400> SEQUENCE: 24
actgcactct tctggtccat gttcttacg gctcgagctg agcttttgct caccgtccac       60
cactgctgtt tgccaccacc gcanacctgc cgctgactcc catccctctg gatcctgcag     120
ggtgtccgct gtgctcctga tccagcgagg cgcccattgc cgctcccaat tgggctaaag    180
gcttgccatt gtncctgcac ggctaagtgc ctgggtttgt tctaattgag ctgaacacta    240
ntcactgggt tccatggttc tcttctgtga cccacggctt ctaatagaac tataacactt    300
accacatggc ccaagattcc attccttgga atccgtgagg gcaagaactc caggtcagag    360
aatacgaggc ttgccaccat cttggaagcg gcctgctacc atcttggaag tggttcacca    420
ccatcttggg agctctgtga gcaaggaccc ccgtaaca ttttggcaac cacgaacgga      480
catccaaagt gatacatcct gggaaggacc ctacccagtc attttatcta ccccaactgc    540
ggttaaagtg gctggagtgg agtcttggat acatcacact tgagtcaaat cctggatact    600
gccaaaggaa cctgaaaatc caggagacaa cgctagctat tcctgtgaac ctctagagga    660
tttgcgcctg ctcttcaaac aacaaccagg aggaaagtaa ctaaaatcat aaatccccat    720
ggccctccct tatcatattt ttctctttac tgttgtttca ccctctttca ctctcactgc    780
acccctccca tgccgctgta tgaccagtag ctcccttac caagagtttc tatggagaat    840
gcagcgtccc ggaaatattg atgccccatc gtataggagt ctttgtaagg gaaccccac     900
```

```
cttcactgcc cacacccata tgccccgcaa ctgctatcac tctgccactc tttgcatgca    960
tgcaaatact cattattgga caggaaaaat gattaatcct agttgtcctg gaggacttgg   1020
agtcactgtc tgttggactt acttcaccca aactggtatg tctgatgggg gtggagttca   1080
agatcaggca agagaaaaac atgtaaaaga agtaatctcc caactcaccc gggtacatgg   1140
cacctctagc ccctacaaag gactagatct ctcaaaacta catgaaaccc tccgtaccca   1200
tactcgcctg gtaagcctat ttaataccac cctcactggg ctccatgagg tctcggccca   1260
aaaccctact aactgttgga tatgcctccc cctgaacttc aggccatatg tttcaatccc   1320
tgtacctgaa caatggaaca acttcagcac agaaataaac accacttccg ttttagtagg   1380
acctcttgtt tccaatctgg aaataaccca tacctcaaac ctcacctgtg taaaatttag   1440
caatactaca tacacaacca actcccaatg catcaggtgg gtaactcctc ccacacaaat   1500
agtctgccta ccctcaggaa tattttttgt ctgtggtacc tcagcctatc gttgtttgaa   1560
tggctcttca gaatctatgt gcttcctctc attcttagtg cccccctatgg ccatctacac   1620 tgaacaagat ttatacagtt atgtcatatc taagccccgc aacaaaagag tacccattct   1680
tccttttgtt ataggagcag gagtgctagg tgcactaggt actggcattg gcggtatcac   1740
aacctctact cagttctact acaaactatc tcaagaacta atggggaca tggaacgggt   1800 cgccgactcc ctggtcacct tgcaagatca acttaactcc ctagcagcag tagtccttca   1860
aaatcgaaga gctttagact tgctaaccgc tgaaagaggg ggaacctgtt tattttttag   1920
ggaagaatgc tgttattatg ttaatcaa                                      1948
```

<210> SEQ ID NO 25
<211> LENGTH: 1136
<212> TYPE: DNA
<213> ORGANISM: Homo sapiens

<400> SEQUENCE: 25

```
ccatggccat ctacactgaa caagatttat acagttatgt catatctaag ccccgcaaca     60
aaagagtacc cattcttcct tttgttatag gagcaggagt gctaggtgca ctaggtactg    120
gcattggcgg tatcacaacc tctactcagt tctactacaa actatctcaa gaactaaatg    180
gggacatgga acgggtcgcc gactccctgg tcaccttgca agatcaactt aactccctag    240
cagcagtagt ccttcaaaat cgaagagctt tagactcgct aaccgctgaa agagggggaa    300 cctgttttatt tttaggggaa gaatgctgtt attatgttaa tcaatccgga atcgtcactg    360
agaaagttaa agaaattcga gatcgaatac aacgtagagc agaagagctt cgaaacactg    420
gaccctgggg cctcctcagc caatggatgc cctggattct cccttctta ggacctctag    480 cagctataat attgctactc ctctttggac cctgtatctt taacctcctt gttaactttg    540
tctcttccag aatcgaagct gtaaaactac aaatggagcc caagatgcag tccaagacta    600
agatctaccg cagacccctg gaccggcctg ctagcccacg atctgatgtt aatgacatca    660
aaggcacccc tcctgaggaa atctcagctg cacaacctct actacgcccc aattcagcag    720
gaagcagtta gagcggtcgt cggccaacct ccccaacagc acttaggttt tcctgttgag    780
atgggggact gagagacagg actagctgga tttcctaggc tgactaagaa tccctaagcc    840
tagctgggaa ggtgaccaca tccacccttta aacacggggc ttgcaactta gttcacacct    900
gaccaatcag agagctcact aaaatgctaa ttaggcaaag acaggaggta aagaaatagc    960
caatcatcta ttgcatgaga gcacagcagg agggacaatg atcgggatat aaacccaagt   1020
```

-continued

| | |
|---|---:|
| cttcgagccg gcaacggcaa cccccttttgg gtcccctccc tttgtatggg agctctgttt | 1080 |
| tcatgctatt tcactctatt aaatcttgca gctgcgaaaa aaaaaaaaaa aaaaaa | 1136 |

<210> SEQ ID NO 26
<211> LENGTH: 2782
<212> TYPE: DNA
<213> ORGANISM: Homo sapiens

<400> SEQUENCE: 26

| | |
|---|---:|
| atgggagctg ttttcatgct atttcactct attaaatctt gcaactgcac tcttctggtc | 60 |
| catgtttctt acggctcgag ctgagctttt gctcaccgtc caccactgct gtttgccacc | 120 |
| accgcagacc tgccgctgac tcccatccct ctggatcctg cagggtgtcc gctgtgctcc | 180 |
| tgatccagcg aagcgcccat tgccgctccc aattgggcta aaggcttgcc attgttcctg | 240 |
| cacggctaag tgcctgggtt tgttctaatt gagctgaaca ctagtcactg ggttccatgg | 300 |
| ttctcttctg tgacccacgg cttctaatag aactataaca cttaccacat ggcccaagat | 360 |
| tccattcctt ggaatccgtg aggccaacga actccaggtc agagaatacg aagcttgcca | 420 |
| ccatcttgga agcggcctgc taccatcttg aagtggttc accaccatct ggggagctct | 480 |
| gtgagcaagg acccccggt gacattttgg cgaccaccaa cggacatccc aagtgataca | 540 |
| tcctgggaag gaccctaccc agtcattta tctaccccaa ctgcggttaa agtggctgga | 600 |
| gtggagtctt ggatacatca cacttgagtc aaatcctgga tactgccaaa ggaacctgaa | 660 |
| aatccaggag acaacgctag ctattcctgt gaacctctag aggatttgcg cctgctcttc | 720 |
| aaacaacaac caggaggaaa gtaactaaaa tcataaatcc ccatgggcct cccttatcat | 780 |
| attttttctct gtagtgttct ttcaccctgt ttcactctca ctgcacccccc tccatgccgc | 840 |
| tgtatgacca gtagctcccc tcacccagag tttctatgga gaatgcagcg tcccggaaat | 900 |
| attgatgccc catcgtatag gagtcttttct aagggaaccc ccaccttcac tgcccacacc | 960 |
| catatgcccc gcaactgcta tcactctgcc actctttgca tgcatgcaaa tactcattat | 1020 |
| tggacaggaa aaatgattaa tcctagttgt cctggaggac ttggagtcac tgtctgttgg | 1080 |
| acttacttca cccaaaactgg tatgtctgat ggggtggag ttcaagatca ggcaagagaa | 1140 |
| aaacatgtaa aagaagtaat ctcccaactc accggggtac atggcacctc tagcccctac | 1200 |
| aaaggactag atctctcaaa actacatgaa ccctccgta cccatactcg cctggtaagc | 1260 |
| ctatttaata ccaccctcac tgggctccat gaggtctcgg cccaaaaccc tactaactgt | 1320 |
| tggatatgcc tccccctgaa cttcaggcca tatgtttcaa tccctgtacc tgaacaatgg | 1380 |
| aacaacttca gcacagaaat aaacaccact tccgttttag taggacctct tgtttccaat | 1440 |
| gtggaaataa cccataccctc aaacctcacc tgtgtaaaat ttagcaatac tacatacaca | 1500 |
| accaactccc aatgcatcag gtgggtaact cctcccacac aaatagtctg cctaccctca | 1560 |
| ggaatatttt ttgtctgtgg tacctcagcc tatcgttgtt tgaatggctc ttcagaatct | 1620 |
| atgtgcttcc tctcattctt agtgccccct atgaccatct acactgaaca agatttatac | 1680 |
| agttatgtca tatctaagcc ccgcaacaaa agagtaccca ttcttccttt tgttataggg | 1740 |
| gcaggagtgc taggtgcact aggtactggc attggcggta tcacaaacctc tactcagttc | 1800 |
| tactacaaac tatctcaaga actaaatggg gacatggaac gggtcgccga ctccctggtc | 1860 |
| accttgcaag atcaacttaa ctccctagca gcagtagtcc ttcgaaatcg aagagcttta | 1920 |
| gacttgctaa ccgctgagag aggggggaacc tgtttatttt taggggaaga atgctgttat | 1980 |
| tatgttaatc aatccggaat cgtcactgag aaagttgaag aaattccaga tcgaatacaa | 2040 |

```
cgtatagcag aggagcttcg aaacactgga ccctggggcc tcctcagccg atggatgccc    2100
tggattctcc ccttcttagg acctctagca gctataatat tgctactcct ctttggaccc    2160
tgtatctttg acctccttgt taactttgtc tcttccagaa tcgaagctgt gaaactacaa    2220
atggagccca agatgcagtc caagactaag atctaccgca gacccctgga ccggcctgct    2280
agcccacgat ctgatgttaa tgacatcaaa ggcacccctc ctgaggaaat ctcagctgca    2340
caacctctac tacgccccaa ttcagcagga agcagttaga gcggtggtcg gccaacctcc    2400
ccaacagcac ttaggttttc ctgttgagat gggggactga gagacaggac tagctggatt    2460
tcctaggctg actaagaatc cttaagccta ggtgggaagg tgaccacatc cacctttaaa    2520
cacggggctt gcaacttagc tcacacctga ccaatcagag agctcactaa aatgctaatt    2580
aggcaaagac aggaggtaaa gaaatagcca atcatttatt gcctgagagc acagcaggag    2640
ggacaatgat cgggatataa acccaagttt tcgagccggc aacggcaacc ccctttgggt    2700
cccctccctt tgtatgggag ctctgttttc atgctatttc actctattaa atcttgcaac    2760
tgcaaaaaaa aaaaaaaaa aa                                              2782

<210> SEQ ID NO 27
<211> LENGTH: 666
<212> TYPE: DNA
<213> ORGANISM: Homo sapiens
<220> FEATURE:
<221> NAME/KEY: misc_feature
<222> LOCATION: (119)..(119)
<223> OTHER INFORMATION: n = a or g or c or t/u

<400> SEQUENCE: 27
tgtccgctgt gctcctgatc cagcgaggcg cccattgccg ctcccaattg ggctaaaggc     60
ttgccattgt tcctgcacgg ctaagtgcct gggtttgttc taattgagct gaacactant    120
cactgggttc catggttctc ttctgtgacc cacggcttct aatataacta taacacttac    180
cacatggccc aagattccat tccttggaat ccgtgaggcc aagaactcca ggtcagagaa    240
tacgaggctt gccaccatct tggaagcggc ctgctaccat cttggaagtg gttcaccacc    300
atcttgggag ctctgtgagc aaggaccccc cggtaacatt ttggcaacca cgaacggaca    360
tccaaagtga atcgaagctg taaaactaca aatggagccc aagatgcagt ccaagactaa    420
gatctaccgc agacccctgg accggcctgc tagcccacga tctgatgtta atgacatcaa    480 aggcaccccct cctgaggaaa tctcagctgc acaacctcta ctacgcccca attcagcagg    540
aagcagttag agcggtcgtc ggccaacctc cccaacagca cttaggtttt cctgttgaga    600
tgggggactg agagacagga ctagctggat ttcctaggct gactaagaat ccctaagcct    660
agctgg                                                               666

<210> SEQ ID NO 28
<211> LENGTH: 3372
<212> TYPE: DNA
<213> ORGANISM: Homo sapiens

<400> SEQUENCE: 28
gacttcccaa ataccagagg aagcagagtg gtttacagtc ctggaccttc aggatgcctt     60
cttctgcatc cctgtacatc ctgactctca attcttgttt gcctttgaag atacttcaaa    120
cccagcatct caactcacct ggactatttt accccaaggg ttcagggata gtccccatct    180
atttggccag gcattagccc aagacttgag ccaatcctca tacctggaca cttgtccttc    240
```

```
ggtaggtgga tgatttactt ttggccgccc attcagaaac cttgtgccat caagccaccc      300
aagcgctctt caatttcctc gctacctgtg gctacatggt ttccaaacca aaggctcaac      360
tctgctcaca gcaggttact tagggctaaa attatccaaa ggcaccaggg ccctcagtga      420
ggaacacatc cagcctatac tggcttatcc tcatcccaaa accctaaagc aactaagggg      480
attccttggc gtaataggtt tctgccgaaa atggattccc aggtatggcg aaatagccag      540
gtcattaaat acactaatta aggaaactca gaaagccaat acccatttag taagatggac      600
aactgaagta gaagtggctt tccaggccct aacccaagcc ccagtgttaa gtttgccaac      660
agggcaagac ttttgttcat atgtcacaga aaaacagga atagctctag gagtccttac      720
acagatccga gggatgagct tgcaacctgt ggcacacctg actaaggaaa ttgatgtagt      780
ggcaaagggt tgacctcatt gtttacgggt agtggtggca gtagcagtct tagtatctga      840
agcagttaaa ataatacagg gaagagatct tactgtgtgg acatctcatg atgtgaatgg      900
catactcact gctaaaggag acttgtggct gtcagacaac tgtttactta aatgtcaggc      960
tctattactt gaagggccag tgctgcgact gtgcacttgt gcaactctta acccagccac     1020
atttcttcca gacaatgaag aaaagataaa acataactgt caacaagtaa tttctcaaac     1080
ctatgccact cgaggggacc ttttagaggt tcctttgact gatcccgacc tcaacttgta     1140
tactgatgga agttcctttg tagaaaaagg acttcgaaaa gtggggtatg cagtggtcag     1200
tgataatgga atacttgaaa gtaatcccct cactccagga actagtgctc agctagcaga     1260
actaatagcc ctcacttggg cactagaatt aggagaagaa aaaagggcaa atataataca     1320
gactctaaat atgcttacct agtcctccat gcccatgcag caatatggaa agaaagggaa     1380
ttcctaactt ctgagagaac acctatcaaa catcaggaag ccattaggaa attattattg     1440
gctgtacaga aacctagaga ggtggcagtc ttacactgcc ggggtcatca caaggaaag     1500 gaaagggaaa tacaagagaa ctgccaagca tatattgaag ccaaaagagc tgcaaggcag     1560
gaccctccat tagaaatgct tattaaactt cccttagtat agggtaatcc cttccgggaa     1620
accaagcccc agtactcagc aggagaaaca gaatggggaa cctcacgagg cagttttctc     1680
ccctcgggac ggttagccac tgaagaaggg aaaatacttt tgcctgcaac tatccaatgg     1740
aaattactta aaaccttca tcaaaccttt cacttaggca tcgatagcac ccatcagatg     1800
gccaaatcat tatttactgg accaggcctt ttcaaaacta tcaagcagat agtcagggcc     1860
tgtgaagtgt gccagagaaa taatcccctg ccttatcgcc aagctccttc aggagaacaa     1920
agaacaggcc attaccctgg agaagactgg caactgtttt tacccacaag cccaaacctc     1980
agggatttca gtatctacta gtctgggtag atactttcac gggttgggca gaggccttcc     2040
cctgtaggac agaaaaggcc caagaggtaa taaaggcact agttcatgaa ataattccca     2100
gattcggact tccccgaggc ttacagagtg acaatagccc tgctttccag gccacagtaa     2160
cccagggagt atcccaggcg ttaggtatac gatatcactt acactgcgcc tgaaggccac     2220
agtcctcagg gaaggtcgag aaaatgaatg aaacactcaa aggacatcta aaaaagcaaa     2280
cccaggaaac ccacctcaca tggcctgttc tgttgcctat agccttaaaa agaatctgca     2340
actttcccca aaaagcagga cttagcccat acgaaatgct gtatggaagg cccttcataa     2400
ccaatgacct tgtgcttgac ccaagacagc caacttagtt gcagacatca cctccttagc     2460
caaatatcaa caagttctta aaacattaca aggaacctat ccctgagaag aggaaaagaa     2520
tattccaccc aagtgacatg gtattagtca agtcccttcc ctctaattcc ccatccctag     2580
atacatcctg ggaaggaccc tacccagtca ttttatctac cccaactgcg gttaaagtgg     2640
```

```
ctggagtgga gtcttggata catcacactt gagtcaaatc ctggatactg ccaaaggaac    2700
ctgaaaatcc aggagacaac gctagctatt cctgtgaacc tctagaggat ttgcgcctgc    2760
tcttcaaaca acaaccagga ggaaaaatcg aagctgtaaa actacaaatg agcccaaga    2820 tgcagtccaa gactaagatc taccgcagac ccctggaccg gcctgttagc ccacgatctg    2880
atgttaatga catcaaaggc acccctcctg aggaaatctc agctgcacaa cctctactac    2940
gccccaattc agcaggaagc agttagagcg gtcgtcggcc aacctcccca acagcactta    3000
ggttttcctg ttgagatggg ggactgagag acaggactag ctggatttcc taggctgatt    3060
aagaatccct aagcctagct gggaaggtga ccacatccac ctttaaacac ggggcttgca    3120
acttagctca cacctgacca atcagagagc tcactaaaat gctaattagg caaagacagg    3180
aggtaaagaa atagccaatc atttattgcc tgagagcaca gcaggaggga caatgatcgg    3240
gatataaacc caagttttcg agccggcaac ggcaaccccc tttgggtccc ctcccttgt    3300 atgggagctc tgttttcatg ctatttcact ctattaaatc ttgcaactgc aaaaaaaaaa    3360
aaaaaaaaaa aa                                                         3372
```

<210> SEQ ID NO 29
<211> LENGTH: 2372
<212> TYPE: DNA
<213> ORGANISM: Homo sapiens
<220> FEATURE:
<221> NAME/KEY: misc_feature
<222> LOCATION: (1191)..(1191)
<223> OTHER INFORMATION: n = a or g or c or t/u
<220> FEATURE:
<221> NAME/KEY: misc_feature
<222> LOCATION: (1213)..(1213)
<223> OTHER INFORMATION: n = a or g or c or t/u
<220> FEATURE:
<221> NAME/KEY: misc_feature
<222> LOCATION: (2089)..(2089)
<223> OTHER INFORMATION: n = a or g or c or t/u
<220> FEATURE:
<221> NAME/KEY: misc_feature
<222> LOCATION: (2274)..(2274)
<223> OTHER INFORMATION: n = a or g or c or t/u

<400> SEQUENCE: 29

```
actgcactct tctggtccat gtttcttacg gctcgagctg agcttttgct caccgtccac     60
cactgctgtt tgccaccacc gcagacctgc cgctgactcc catccctctg atcctgcag     120 ggtgtccgct gtgctcctga tccagcgagg cgcccattgc cgctcccaat gggctaaag     180 gcttgccatt gttcctgcac ggctaagtgc ctgggtttgt tctaattgag ctgaacacta    240
atcactgggt tccatggttc tcttctgtga cccacggctt ctaatagaac tataacactt    300
accacatggc ccaagattcc attccttgga atccgtgagg ccaagaactc caggtcagag    360
aatacgaggc ttgccaccat cttggaagcg gcctgctacc gtcttggaag tggttcacca    420
ccatcttggg agctctgtga gcaaggaccc cccggtaaca ttttggcaac caacgacgga    480
catccaaagt gatgggaaac gttccccgca agacaaaaac gcccctaaga cgtattctgg    540
agaattggga ccaatttgac cctcagacac taagaaagaa acgacttata ttcttctgca    600
gtgccgcctg gcactcctga gggaagtata aattataaca ccatcttaca gctagacctc    660
ttttgtagaa aaggcaaatg gagtgaagtg ccataagtac aaactttctt ttcattaaga    720
gacaactcac aattatgtaa aaagtgtgat ttatgcccta caggaagcct tcagagtcta    780
cctccctatc ccagcatccc cgactccttc cccaactaat aaggaccccc cttcaaccca    840
```

-continued

```
aatggtccaa aaggagatag acaaaagggt aaacagtgaa ccaaagagtg ccaatattcc    900
ccaattatga cccctccaag cagtgggagg aagagaattc ggcccagcca gagtgcatgt    960
gccttttct ctcccagact taaagcaaat aaaaacagac ttaggtaaat tctcagataa    1020
ccctgatggc tatattgatg ttttacaagg gttaggacaa ttctttgatc tgacatggag    1080
agatataatg tcactgctaa atcagacact aaccccaaat gagagaagtg ccaccataac    1140
tgcagcctga gggtttggcg tctctggtat ctcagtcagg tcaatggata nggatgacaa    1200
cagaaggaaa ganaatgatt ccccacaggc cagcaggcag ttcccagtct agaccctcat    1260
tgggacacag aatcagaaca tggagattgg tgctgcagac atttgctaac ttgtgtgcta    1320
gaaggactaa ggaaaactag gaagaagtct atgaattact caatgatgtc caccataaca    1380
cagggaaggg aagaaaatcc tactgccttt ctggagagac taagggaggc attgaggaag    1440
cgtgcctctc tgtcacctga ctcttctgaa ggccaactaa tcttaaagcg taagtttatc    1500
actcagtcag ctgcagacat tagaaaaaac ttcaaaagtc tgccgtaggc ccggagcaaa    1560
acttagaaac cctattgaac ttggcaacct cggttttta taatagagat caggaggagc    1620
aggcggaaca ggacaaacgg gattaaaaaa aaggccaccg ctttagtcat gaccctcagg    1680
caagtggact ttggaggctc tggaaaaggg aaaagctggg caaattgaat gcctaatagg    1740
gcttgcttcc agtgcggtct acaaggacac tttaaaaaag attgtccaag tagaagtaag    1800
ccgccccttc gtccatgccc cttatttcaa gggaatcact ggaaggccca ctgccccagg    1860
ggacaaaggt cttttgagtc agaagccact aaccagatga tccagcagca ggactgaggg    1920
tgcctggggc aagcgccatc ccatgccatc accctcacag agccctgggt atgcttgacc    1980
attgagggcc aggaaggttg tctcctggac actggtgcgg tcttcttagt cttactcttc    2040
tgtcccggac aactgtcctc cagatctgtc actattctga gggggtccnt aagacgggca    2100
gtcactagta acttttcccc agccactaag ttatgaactg gggagcttta ttcttttcac    2160
atgctttct aattatgctt gaaagcccca ctaccttgtt agggagagac attctagcaa    2220
aagcaggggc cattatacac ctgaacatag gagaaggaac acccgtttgt tgtncccctg    2280
cttgaggaag gaattaatcc tgaagtctgg gcaacagaag gacaatatgg acgagccaaa    2340
gaatgcccgt cctgttcaag ttaaactaaa gg                                  2372
```

```
<210> SEQ ID NO 30
<211> LENGTH: 7582
<212> TYPE: DNA
<213> ORGANISM: Homo sapiens
<220> FEATURE:
<221> NAME/KEY: misc_feature
<222> LOCATION: (198)..(198)
<223> OTHER INFORMATION: n = a or g or c or t/u
<220> FEATURE:
<221> NAME/KEY: misc_feature
<222> LOCATION: (307)..(307)
<223> OTHER INFORMATION: n = a or g or c or t/u
<220> FEATURE:
<221> NAME/KEY: misc_feature
<222> LOCATION: (355)..(355)
<223> OTHER INFORMATION: n = a or g or c or t/u
<220> FEATURE:
<221> NAME/KEY: misc_feature
<222> LOCATION: (1309)..(1309)
<223> OTHER INFORMATION: n = a or g or c or t/u
<220> FEATURE:
<221> NAME/KEY: misc_feature
<222> LOCATION: (1331)..(1331)
<223> OTHER INFORMATION: n = a or g or c or t/u
<220> FEATURE:
<221> NAME/KEY: misc_feature
```

```
<222> LOCATION: (2213)..(2213)
<223> OTHER INFORMATION: n = a or g or c or t/u
<220> FEATURE:
<221> NAME/KEY: misc_feature
<222> LOCATION: (2398)..(2398)
<223> OTHER INFORMATION: n = a or g or c or t/u
<220> FEATURE:
<221> NAME/KEY: misc_feature
<222> LOCATION: (3787)..(3787)
<223> OTHER INFORMATION: n = a or g or c or t/u
<220> FEATURE:
<221> NAME/KEY: misc_feature
<222> LOCATION: (4115)..(4115)
<223> OTHER INFORMATION: n = a or g or c or t/u
<220> FEATURE:
<221> NAME/KEY: misc_feature
<222> LOCATION: (4261)..(4261)
<223> OTHER INFORMATION: n = a or g or c or t/u

<400> SEQUENCE: 30
```

| | | | | | |
|---|---|---|---|---|---|
| caacaatcgg | gatataaacc | caggcattcg | agctggcaac | agcagccccc | ctttgggtcc | 60 |
| cttccctttg | tatgggagct | gttttcatgc | tatttcactc | tattaaatct | tgcaactgca | 120 |
| ctcttctggt | ccatgtttct | tacggctcga | gctgagcttt | tgctcaccgt | ccaccactgc | 180 |
| tgtttgccac | caccgcanac | ctgccgctga | ctcccatccc | tctggatcct | gcagggtgtc | 240 |
| cgctgtgctc | ctgatccagc | gargcgccca | ttgccgctcc | caattgggct | aaaggcttgc | 300 |
| cattgtncct | gcacggctaa | gtgcctgggt | ttgttctaat | tgagctgaac | actantcact | 360 |
| gggttccatg | gttctcttct | gtgacccacg | gcttctaata | kaactataac | acttaccaca | 420 |
| tggcccaaga | ttccattcct | tggaatccgt | gaggscaacg | aactccaggt | cagagaatac | 480 |
| gargcttgcc | accatcttgg | aagcggcctg | ctaccrtctt | ggaagtggtt | caccaccatc | 540 |
| ttgggagctc | tgtgagcaag | gaccccccgg | tracattttg | gcraccamsr | acggacatcc | 600 |
| maagtgatgg | gaaacgttcc | ccgcaagaca | aaaacgcccc | taagacgtat | tctggaraat | 660 |
| tgggamcaat | ttgaccctca | gacactaaga | aagaaacgac | ttatattctt | ctgcagtgcc | 720 |
| gcctggcact | cctgagggaa | gtataaatta | taacaccatc | ttacagctag | acytcttttg | 780 |
| tagaaaaggc | aaatggagtg | aagtgccata | agtacaaact | ttcttttcat | taagagacaa | 840 |
| ctcacaatta | tgtaaaaagt | gtgatttatg | ccctacagga | agccttcaga | gtctacctcc | 900 |
| ctatcccagc | atcccccgact | ccttccccam | ytaataagga | ccccccttca | acccaaatgg | 960 |
| tccaaaagga | gatagacaaa | agggtaaaca | gtgaaccaaa | gagtgccaat | attccccaat | 1020 |
| tatgacccct | cccaagcagt | gggaggaaga | gaattcggcc | cagccagagt | gcatgtgcyt | 1080 |
| tttyytctcc | cagacttaaa | gcaaataaaa | acagacttag | gtaaattctc | agataaycct | 1140 |
| gatggctata | ttgrtgtttt | acaagggtta | ggacaattct | ttgatctgac | atggagagat | 1200 |
| atatatgtca | ctgctaaatc | agacactaac | cccaaatgag | agaagtgcca | ccataactgc | 1260 |
| agcctgagrg | tttggcgatc | tctggtatct | cagtcaggtc | aatggatang | gatgacaaca | 1320 |
| gaaggaaaga | naatgattcc | ccacaggcca | gcargcagtt | cccagtctas | accctcattg | 1380 |
| gggacacaga | aatcagtaac | atgggagatt | ggtgctgcag | acatttgcta | acttgtgtgc | 1440 |
| tasaaggact | aaggaaaact | asgaagaaar | tctaygaatt | actcaatgat | gtccaccata | 1500 |
| acacagggga | agggaagaaa | atcctactgc | ctttctggag | agactaaggg | aggcattgag | 1560 |
| gaagcgtgcc | tctctgtcac | ctgactcttc | tgaaggccaa | ctaatcttaa | agcgtaagtt | 1620 |
| tatcactcag | tcagctgcag | acattagaaa | aaacttcaaa | agtctgccgt | aggcccggag | 1680 |
| caaaacttag | aaaccctatt | gaacttggca | acytcggttt | tttataatag | agatcaggag | 1740 |

```
gagcaggcgg aacaggacaa acgggattaa aaaaaaggcc accgctttag tcatgaccct    1800
caggcaagtg gactttggag gctctggaaa agggaaaagc tgggcaaatt gaatgcctaa    1860
tagggcttgc ttccagtgcg gtctacaagg acactttaaa aaagattgtc caagtagaag    1920
taagccgccc cttcgtccat gccccttatt tcaagggaat cactggaagg cccactgccc    1980
caggggacaa aggtcttttg agtcagaagc cactaaccag atgatccagc agcaggactg    2040
agggtgcctg gggcaagcgc catcccatgc catcaccctc acagagccct gggtatgctt    2100
gaccattgag ggccaggaag gttgtctcct ggacactggt gcggtcttct tagtcttact    2160
cttctgtccc ggacaactgt cctccagatc tgtcactatt ctgagggggt ccntaagacg    2220
ggcagtcact agatacttty tcccagccac taagttatga actggggagc tttattcttt    2280
tcacatgctt ttctaattat gcttgaaagc cccactacct tgttagggag agacattcta    2340
gcaaaagcag gggccattat acacctgaac ataggagaag gaacaccgt ttgttgtncc     2400 cctgcttgag gaaggaatta atcctgaagt ctgggcaaca gaaggacaat atggacgagc    2460
caaagaatgc ccgtcctgtt caagttaaac taaaggattc cacttccttt ccctaccaaa    2520
ggcagtaccc cctcagaccc aaggcccaac aaggattcca aaagattgtt aaggacttaa    2580
aagcccaagg cttagtaaaa ccatgcataa ctccctgcag taattccgta gtggattgag    2640
gaggcacaga aacccagtgg acagtggagg gttagtgcaa gatctcagga ttatcaatgg    2700
aggccgttgt cctttttatac ccagctgtac ctagcccta tactgtgmyt tcccaaatac    2760
cagaggaagc agagtggttt acastcctgg accttmagga tgccttcttc tgcatccctg    2820
tacatcctga ctctcaattc ttgtttgcct ttgaagatac ttcaaaccca rcatctcaac    2880
tcacctggac trttttaccc caagggttca gggatagycc ccatctatt ggccaggcat     2940 tagcccaaga cttgagycar tymtcatacc tggacactct tgtccttcrg takgtggatg    3000 atttacttt rgcygccyrt tcagaaacct tgtgccatca agccaccaa gcrctcttma      3060 atttcctcgc yacctgtggc tacawggttt ccaaacsara rgctcarctc tgctcacagc    3120
aggttaaata cttaggrcta arattatcca aaggcaccar ggccctcagt gaggaayrya    3180
tccagcctat actggcttat cctcatcyca aaaccctaaa gcaactaagr grrttccttg    3240
gcrtaayagg yttctgccga awatggattc cccaggtwtg gcraaatagc caggycatta    3300
watacastaa ttaaggaaac tcagaaagcc aatacccatt tartaagatg gayamctgaa    3360
gymraagtgg ctttccaggc ccctaaagaa ggccttaaac ccaagcccca gtgttaagyt    3420
tgccaacrgg gcaagacttt tsttyatayr tcacagaaaa aaacagraay agctctrgga    3480
gtccttacac agrtccragg gaygagcttg caaccyrtgg cryacctgas taaggaaayt    3540
gatgtagtgg caaagggttg rcytcattgt ttaygggtag tggtggcagt agcagtykta    3600
gtatctgaag cagttaaaat aatacagggr agagatctta ctgtgtggac atctcatgak    3660
gtgaayrgca tactcactgc taaaggagac ttgtggctgt cagacaacyg tttacttaaa    3720
trtcaggctc tattacttga arggccagtg ctgcractgt gcacttgtgc aactcttaac    3780
ccagycncat ttcttccaga caatgaagaa aagataraay ataactgtca acaartaatt    3840
tctcaaacct atgccactcg aggggacctt ytagargttc cyttgactga tccygacctt    3900
caacttgtat actgatggaa gttccttttgt agaaaaagga cttcgaaaag yggggtatgc    3960
agtggtcagt gataatggaa tayttgaaag taatcccctc actccaggaa ctagtgctya    4020
gctrgcagaa ctaatagccy tcaytkgggc actagaatta ggagaagraa aaagggyaaa    4080
tatatataca gactctrart atgctyacct agtcntccat gcccatgmrg caatatgsar    4140
```

```
agaaagggaa ttcctaactt cygagrgaac acctatcama catcaggaag ccattaggar    4200
attattaytg gcwgtacaga aacctaraga ggtggmagtc ttacactgcy ggggtcatca    4260
naaaggaaag raaagggaaa tasaagrgaa ytgccaagca katattgaag cmaaaagagc    4320
tgcaaggcag gaccctccat tagaaatgct tattaaactt cccttagtat agggtaatcc    4380
cttccgggaa accaagcccc agtactcagc aggagaaaca gaatgggaa cctcacgagg     4440 cagttttctc ccctcgggac ggttagccac tgaagaaggg aaaatacttt tgcctgcaac    4500
tatccaatgg aaattactta aaacccttca tcaaaccttt cacttaggca tcgatagcac    4560
ccatcaratg gccaaatcat tatttactgg accaggcctt ttcaaaacta tcaagcarat    4620
aktcagggcc tgtgaaktgt gccararaaa taatcccctg cctyatcgcc aagctccttc    4680
aggaraacaa araacaggcc attaccctgr araaractgg caactgattt tacccacaag    4740
cccaaacctc agggatttca gtatctacta gtctgggtar atactttcac gggttgggca    4800
raggccttcc cctgtaggac agaaaaggcc caagaggtaa taaaggcact agttcatgaa    4860
ataattccca gattcggact tccccgaggc ttacagagtg acaatagccc tgcttttccag   4920 gccacagtaa cccagggagt atcccaggcg ttaggtatac gatatcactt acactgcgcc    4980
tgaaggccac agtcctcagg gaaggtcgag aaaatgaatg aaayactcaa aggacatcta    5040
aaaaagcaaa cccaggaaac ccacctcaca tggcctgytc tgttgcctat agccttaaaa    5100
agaatctgca acttttcccca aaaagcagga cttagcccat acgaaatgct gtatggaagg    5160
cccttcataa ccaatgacct tgtgcttgac ccaagacagc caacttagtt gcagacatca    5220
cctccttagc caaatatcaa caagttctta aaacattaca aggaacctat ccctgagaag    5280
agggaaaaga actattccac ccwwgtgaca tggtattagt caagtccctt cyctctaatt    5340
ccccatccct agatacatcc tgggaaggac cctacccagt catttatyt accccaactg     5400 cggttaaagt ggctggagtg gagtcttgga tacatcacac ttgagtcaaa tcctggatac    5460
tgccaaagga acctgaaaat ccaggagaca acgctagcta ttcctgtgaa cctctagagg    5520
atttgcgcct gctcttcaaa caacaaccag gaggaaagta actaaaatca taaatccccc    5580
atggscctcc cttatcatat tttctctkt astgttsttt yaccctsttt cactctcact     5640
gcaccccctc catgccgctg tatgaccagt agctcccty accmagagtt tctatggaga     5700
atgcagcgtc ccggaaatat tgatgcccca tcgtatagga gtctttstaa gggaaccccc    5760
accttcactg cccacaccca tatgcccgc aactgctatc actctgccac tctttgcatg     5820
catgcaaata ctcattattg gacaggaaaa atgattaatc ctagttgtcc tggaggactt    5880
ggagtcactg tctgttggac ttacttcacc caaactggta tgtctgatgg gggtggagtt    5940
caagatcagg caagagaaaa acatgtaaaa gaagtaatct cccaactcac csgggtacat    6000
ggcacctcta gccctacaa aggactagat ctctcaaaac tacatgaaac cctccgtacc     6060
catactcgcc tggtaagcct atttaatacc accctcactg ggctccatga ggtctcggcc    6120 caaaaccta ctaactgttg gatatgcctc cccctgaact tcargccata tgtttcaatc     6180
cctgtacctg aacaatggaa caacttcagc acagaaataa acaccacttc cgttttagta    6240
ggacctcttg tttccaatst ggaaataacc catacctcaa acctcacctg tgtaaaattt    6300
agcaatacta catcacacaac caactcccaa tgcatcaggt gggtaactcc tcccacacaa   6360
atagtctgcc tacccctcagg aatatttttt gtctgtggta cctcagccta tcgttgtttg   6420
aatggctctt cagaatctat gtgcttcctc tcattcttag tgccccyat grccatctac     6480
```

-continued

```
actgaacaag atttatacag ttatgtcata tctaagcccc gcaacaaaag agtacccatt    6540
cttccttttg ttataggagc aggagtgcta ggtgcactag gtactggcat tggcggtatc    6600
acaacctcta ctcagttcta ctacaaacta tctcaagaac taaatgggga catggaacgg    6660
gtcgccgact ccctggtcac cttgcaagat caacttaact ccctagcagc agtagtcctt    6720
craaatcgaa gagctttaga ctygctaacc gctgaragag ggggaacctg tttatttta    6780 ggggaagaat gctgttatta tgttaatcaa tccggaatcg tcactgagaa agttraagaa    6840
attcsagatc gaatacaacg takagcagar gagcttcgaa acactggacc ctggggcctc    6900
ctcagccrat ggatgccctg gattctcccc ttcttaggac tctagcagc tataatattg     6960 ctactcctct ttggaccctg tatctttrac ctccttgtta actttgtctc ttccagaatc    7020
gaagctgtra aactacaaat ggagcccaag atgcagtcca agactaagat ctaccgcaga    7080
cccctggacc ggcctgytag cccacgatct gatgttaatg acatcaaagg caccctcct    7140 gaggaaatct cagctgcaca acctctacta cgccccaatt cagcaggaag cagttagagc    7200
ggtsgtcggc caacctcccc aacagcactt aggttttcct gttgagatgg gggactgaga    7260
gacaggacta gctggatttc ctaggctgay taagaatccy taagcctags tgggaaggtg    7320
accacatcca cctttaaaca cggggcttgc aacttagytc acacctgacc aatcagagag    7380
ctcactaaaa tgctaattag gcaaagacag gaggtaaaga aatagccaat catytattgc    7440
mtgagagcac agcaggaggg acaatgatcg ggatataaac ccaagtyttc gagccggcaa    7500 cggcaaccc ctttgggtcc cctcccttg tatgggagct ctgttttcat gctatttcac      7560
tctattaaat cttgcarctg cr                                             7582
```

<210> SEQ ID NO 31
<211> LENGTH: 363
<212> TYPE: PRT
<213> ORGANISM: Homo sapiens

<400> SEQUENCE: 31

```
Met Gly Asn Ile Pro Pro Lys Ala Lys Thr Pro Leu Arg Cys Ile Leu
1               5                   10                  15

Glu Asn Trp Asp Gln Cys Asp Thr Gln Thr Leu Arg Lys Lys Arg Phe
            20                  25                  30

Ile Phe Phe Cys Ser Thr Ala Trp Pro Gln Tyr Pro Leu Gln Gly Arg
        35                  40                  45

Glu Thr Trp Leu Pro Glu Gly Ser Ile Asn Tyr Asn Ile Ile Leu Gln
    50                  55                  60

Leu Asp Leu Phe Cys Arg Lys Glu Gly Lys Trp Ser Glu Val Pro Tyr
65                  70                  75                  80

Val Gln Thr Phe Phe Ser Leu Arg Asp Asn Ser Gln Leu Cys Lys Lys
                85                  90                  95

Cys Gly Leu Cys Pro Thr Gly Ser Pro Gln Ser Pro Pro Tyr Pro
            100                 105                 110

Ser Val Pro Pro Thr Pro Ser Ser Thr Asn Lys Asp Pro Pro Leu
        115                 120                 125

Thr Gln Thr Val Gln Lys Glu Ile Asp Lys Gly Val Asn Asn Glu Pro
    130                 135                 140

Lys Ser Ala Asn Ile Pro Arg Leu Cys Pro Leu Gln Ala Val Arg Gly
145                 150                 155                 160

Gly Glu Phe Gly Pro Ala Arg Val Pro Val Pro Phe Ser Leu Ser Asp
                165                 170                 175
```

```
Leu Lys Gln Ile Lys Ile Asp Leu Gly Lys Phe Ser Asp Asn Pro Asp
            180             185             190

Gly Tyr Ile Asp Val Leu Gln Gly Leu Gly Gln Ser Phe Asp Leu Thr
        195             200             205

Trp Arg Asp Ile Met Leu Leu Asn Gln Thr Leu Thr Pro Asn Glu
    210             215             220

Arg Ser Ala Ala Val Thr Ala Ala Arg Glu Phe Gly Asp Leu Trp Tyr
225             230             235             240

Leu Ser Gln Val Asn Asn Arg Met Thr Thr Glu Glu Arg Thr Thr Pro
            245             250             255

Thr Gly Gln Gln Ala Val Pro Ser Val Asp Pro His Trp Asp Thr Glu
            260             265             270

Ser Glu His Gly Asp Trp Cys His Lys His Leu Leu Thr Cys Val Leu
            275             280             285

Glu Gly Leu Arg Lys Thr Arg Lys Lys Pro Met Asn Tyr Ser Met Met
        290             295             300

Ser Thr Ile Thr Gln Gly Lys Glu Glu Asn Pro Thr Ala Phe Leu Asp
305             310             315             320

Arg Leu Arg Glu Ala Leu Arg Lys His Thr Ser Leu Ser Pro Asp Ser
            325             330             335

Ile Glu Gly Gln Leu Ile Leu Lys Asp Lys Phe Ile Thr Gln Ser Ala
            340             345             350

Ala Asp Ile Arg Lys Asn Phe Lys Ser Leu Pro
            355             360

<210> SEQ ID NO 32
<211> LENGTH: 20
<212> TYPE: DNA
<213> ORGANISM: Homo sapiens

<400> SEQUENCE: 32
atccaaagtg gtgagtaata                                               20

<210> SEQ ID NO 33
<211> LENGTH: 20
<212> TYPE: DNA
<213> ORGANISM: Homo sapiens

<400> SEQUENCE: 33
cttttttcag atgggaaacg                                               20
```